(12) United States Patent
Ozawa et al.

(10) Patent No.: US 11,975,086 B2
(45) Date of Patent: *May 7, 2024

(54) METHOD FOR REMOVING KERATOTIC PLUGS

(71) Applicant: KAO CORPORATION, Tokyo (JP)

(72) Inventors: Toshiaki Ozawa, Setagaya-ku (JP); Takaya Sakai, Wakayama (JP); Mariko Miyoshi, Sumida-ku (JP); Daisuke Furukawa, Wakayama (JP); Aya Shirai, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/809,661

(22) Filed: Jun. 29, 2022

(65) Prior Publication Data

US 2022/0347072 A1    Nov. 3, 2022

Related U.S. Application Data

(63) Continuation of application No. 16/604,019, filed as application No. PCT/JP2018/014941 on Apr. 9, 2018, now Pat. No. 11,406,576.

(30) Foreign Application Priority Data

Apr. 9, 2018   (WO) ............... PCT/JP2018/014941

(51) Int. Cl.

| A61K 8/41 | (2006.01) |
| A61K 8/36 | (2006.01) |
| A61K 8/37 | (2006.01) |
| A61K 8/39 | (2006.01) |
| A61K 8/44 | (2006.01) |
| A61K 8/46 | (2006.01) |
| A61K 8/49 | (2006.01) |
| A61K 31/075 | (2006.01) |
| A61K 31/08 | (2006.01) |
| A61K 31/133 | (2006.01) |
| A61K 31/198 | (2006.01) |
| A61K 31/225 | (2006.01) |
| A61K 31/23 | (2006.01) |
| A61K 31/231 | (2006.01) |
| A61K 31/25 | (2006.01) |
| A61K 31/351 | (2006.01) |
| A61K 31/5375 | (2006.01) |
| A61K 45/06 | (2006.01) |
| A61P 17/00 | (2006.01) |
| A61P 17/10 | (2006.01) |
| A61Q 19/00 | (2006.01) |
| A61Q 19/10 | (2006.01) |

(52) U.S. Cl.
CPC ............... *A61K 8/41* (2013.01); *A61K 8/361* (2013.01); *A61K 8/37* (2013.01); *A61K 8/375* (2013.01); *A61K 8/39* (2013.01); *A61K 8/44* (2013.01); *A61K 8/463* (2013.01); *A61K 8/466* (2013.01); *A61K 8/49* (2013.01); *A61K 8/498* (2013.01); *A61K 31/075* (2013.01); *A61K 31/08* (2013.01); *A61K 31/133* (2013.01); *A61K 31/198* (2013.01); *A61K 31/225* (2013.01); *A61K 31/23* (2013.01); *A61K 31/231* (2013.01); *A61K 31/25* (2013.01); *A61K 31/351* (2013.01); *A61K 31/5375* (2013.01); *A61K 45/06* (2013.01); *A61P 17/00* (2018.01); *A61P 17/10* (2018.01); *A61Q 19/00* (2013.01); *A61Q 19/10* (2013.01); *A61K 2800/596* (2013.01)

(58) Field of Classification Search
None
See application file for complete search history.

(56) References Cited

U.S. PATENT DOCUMENTS

| 6,106,857 | A | 8/2000 | Crotty et al. |
| 6,174,536 | B1 | 1/2001 | Crotty et al. |
| 11,406,849 | B2 * | 8/2022 | Abe .................. A61K 8/49 |
| 2006/0008538 | A1 | 1/2006 | Wu et al. |
| 2006/0247146 | A1 * | 11/2006 | Greenberg .......... C11D 11/0052 510/421 |
| 2010/0166886 | A1 | 7/2010 | Wu et al. |
| 2010/0324269 | A1 | 12/2010 | Shultz et al. |
| 2020/0121577 | A1 | 4/2020 | Abe |
| 2020/0155433 | A1 | 5/2020 | Abe |
| 2020/0155434 | A1 | 5/2020 | Abe |
| 2021/0101029 | A1 | 4/2021 | Abe |

FOREIGN PATENT DOCUMENTS

| CN | 101213282 | 7/2008 |
| CN | 103857378 A | 6/2014 |
| CN | 104066421 | 9/2014 |

(Continued)

OTHER PUBLICATIONS

English translation for JP 2014-58499 A (Year: 2014).*

(Continued)

*Primary Examiner* — Sin J Lee

(74) *Attorney, Agent, or Firm* — Oblon, McClelland, Maier & Neustadt, L.L.P.

(57) ABSTRACT

A method for removing keratotic plugs capable of sufficiently exhibiting an excellent keratotic plug-removing effect without a burden, such as pam and of irritation, on the skin. The method comprises applying a composition comprising (X) one or more selected from (X1) 2-amino-2-hydroxymethyl-1,3-propanediol, (X2) 2-amino-2-methyl-1-propanol, and (X3) 2-amino-2-methyl-1,3-propanediol and a nonionic surfactant to the skin.

14 Claims, 1 Drawing Sheet

(56) References Cited

FOREIGN PATENT DOCUMENTS

| | | |
|---|---|---|
| EP | 2 821 053 A1 | 1/2015 |
| JP | 11-12127 A | 1/1999 |
| JP | 11-322570 A | 11/1999 |
| JP | 2002-12512 A | 1/2002 |
| JP | 2002-60313 A | 2/2002 |
| JP | 2002-506015 A | 2/2002 |
| JP | 2003-221328 A | 8/2003 |
| JP | 2004-75575 A | 3/2004 |
| JP | 2005-528323 A | 9/2005 |
| JP | 2007-230929 A | 9/2007 |
| JP | 2011-12252 A | 1/2011 |
| JP | 2013-166746 A | 8/2013 |
| JP | 2013-221020 A | 10/2013 |
| JP | 2014-58499 A | 4/2014 |
| JP | 2014-129278 A | 7/2014 |
| JP | 2015-113307 A | 6/2015 |
| JP | 2016-28065 A | 2/2016 |
| JP | 2016-210751 A | 12/2016 |
| JP | 2018-177778 A | 11/2018 |
| JP | 2018-177779 A | 11/2018 |
| JP | 2018-177780 A | 11/2018 |
| JP | 2018-177781 A | 11/2018 |
| WO | WO 98/17265 A1 | 4/1998 |
| WO | WO 2015/181789 A1 | 12/2015 |
| WO | WO-2018190264 A1 * | 10/2018 ............... A61K 8/36 |

OTHER PUBLICATIONS

English translation for JP 2016-210751 (Year: 2016).*
English translation for DESCRIPTION of WO 2018/190264 A1 (2018).*
English translation for claims of WO 2018/190264 A1 (2018).*
English translation for JP2013-221020 A (2013).*
A product sheet for "Tritontm X-45 Surfactant" obtained from the webpage: https://www.dow.com/en-us/pdp.triton-x-45-surfactant.85765z.html#properties (date unknown).*
A product sheet for "Tritontm X-114 Surfactant" obtained from the webpage: https://www.dow.com/en-us/pdp.triton-x-114-surfactant.85738z.html?productCatalogFlag=1#properties (date unknown).*
A product sheet for Alkyl naphthalene sulfonate sodium salt (obtained from the website: https://www.sigmaaldrich.com/us/en/product/aldrich/916994 (date unknown).*
International Search Report dated Jun. 19, 2018 in PCT/JP2018/014941 filed Apr. 9, 2018.
Machine-assisted English translation for JP 2013-221020A (Year: 2013).
Machine-assisted English translation for JP 2016210751A (Year: 2016).
Extended European Search Report dated Dec. 14, 2020 in corresponding European Patent Application No. 18784620.9, 11 pages.
Daimon Kazuo, "Correct skin beauty and skin care—Wrong maintenance methods will harm your skin", China Machine Press, Oct. 31, 1994, p. 40 (with machine translation) 5 pages.
Sang Chu, "Your Images Is Ten Million: Doing the Best of Yourself", Beijing United Publishing Co., Ltd., Feb. 28, 2017, p. 143 (with machine—generated English abstract(concise explanation)) 4 pages.
"Safety and Technical Standards for Cosmetics", 2015 year edition, National Medical Products Administration, pp. 15 and 47, May 28, 2021 (with machine translation) (this NPL is cited in Chinese Decision of Rejection issued Jan. 19, 2023, Client received the same on Feb. 10, 2023).
Moisture Treatment Lotion, ID 3075733, Mintel GNPD[online], Mar. 2015, Retrieved on Jan. 18, 2024, URL: https://www.portal.mintel.com 6 pages.

* cited by examiner

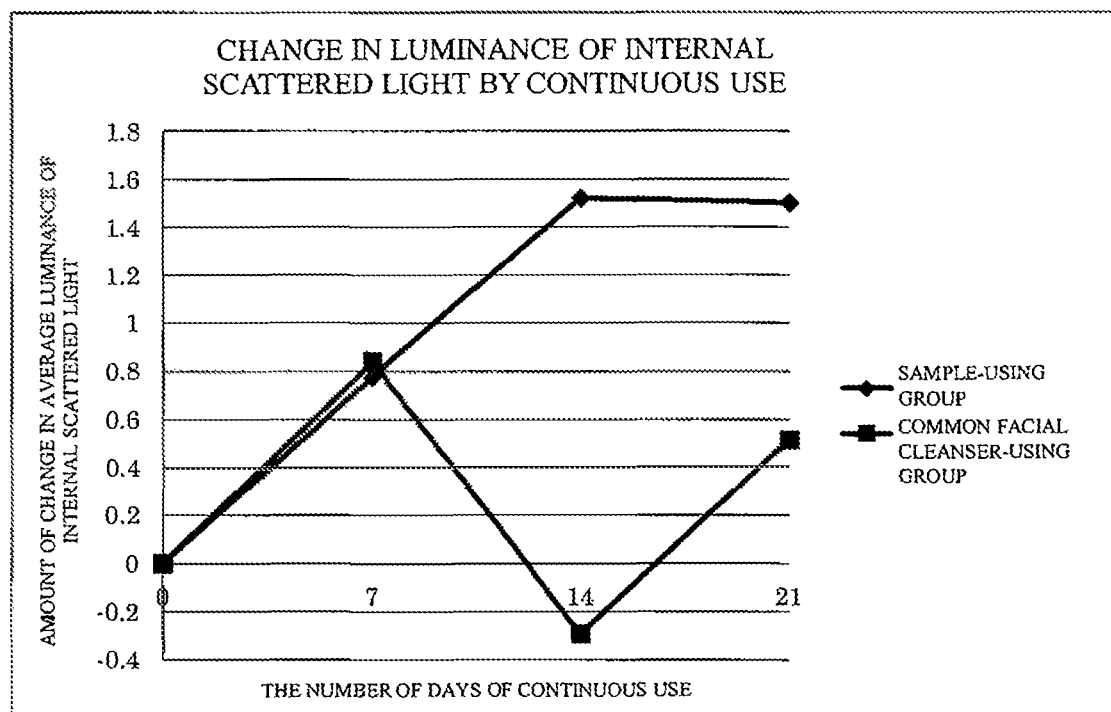

METHOD FOR REMOVING KERATOTIC PLUGS

The present application is continuation of U.S. application Ser. No. 16/604,019, filed Oct. 9, 2019, which is the National Stage of International Application no. PCT/JP2018/014941, filed Apr. 9, 2018, which claims priority to Japanese PCT Application No. PCT/JP2017/014731, filed Apr. 10, 2017. The contents of these applications are incorporated herein by reference in their entireties.

FIELD OF THE INVENTION

The present invention relates to a method for removing keratotic plugs comprising using a composition comprising 2-amino-2-hydroxymethyl-1,3-propanediol or the like.

BACKGROUND OF THE INVENTION

Keratotic plugs are observed in the pores at sites with increased sebum secretion, for example, around the nose, and are a substance occluding the pores like plugs.

If such keratotic plugs are left without being removed, roughness will appear on the skin, and the keratotic plugs physically expand the pores to readily enlarge the openings of the pores. In addition, the surfaces of the keratotic plugs are also darkened by oxidation, leading to a risk of spoiling the beauty appearance. Furthermore, these cause, for example, acne to readily result in skin troubles such as rashes and pimples. Based on these facts, keratotic plugs bother many women as one of causes of pore conspicuousness. Accordingly, a variety of techniques for removing such keratotic plugs have been conventionally developed.

For example, Patent Literature 1 discloses a skin-cleansing agent composition containing an organic acid, such as lactic acid, and a N-acyl taurine anionic surfactant and having a pH of 3 to 5, the composition being capable of exhibiting a keratotic plug-removing effect while providing good foaming and so on. Patent Literature 2 discloses a detergent composition containing a specific nonionic surfactant, an oil agent having a viscosity of 15 mPa·s or less at 30° C., a water-soluble polymer and so on. Patent Literature 3 discloses a facial cleanser containing a dibasic acid diester having 6 to 20 carbon atoms. In all of these, the function of removing keratotic plugs is achieved by specific oil agents.

In contrast, Patent Literature 4 discloses a sheet pack composed of a multi-layer moisture-permeable support and a cosmetic containing a polymer compound having a salt-forming group, such as a carboxyl group. Such a sheet pack is applied onto the skin to impart a smooth feeling, a moist feeling, etc. to the skin and also can exhibit a keratotic plug-removing effect when peeled off from the skin.

(Patent Literature 1) JP-A-2015-113307
(Patent Literature 2) JP-A-2011-12252
(Patent Literature 3) JP-A-2007-230929
(Patent Literature 4) JP-A-H11-12127

SUMMARY OF THE INVENTION

The present invention relates to a method for removing keratotic plugs using a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

The present invention also relates to a keratotic plug-removing composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

In the skin detergent composition described in Patent Literature 1, only the liquid sebum, desquamation, and partially protruding keratotic plugs on the skin are removed mainly by the detergency of the anionic surfactant. In the detergent compositions described in Patent Literatures 2 and 3 each showing the effect of removing keratotic plugs, for example, by a specific oil, only a part of keratotic plugs in a state of being easily removed is removed mainly by the solubility of the oil. These compositions are not techniques capable of directly removing the dirt in pores, and improvement is still necessary for sufficiently removing keratotic plugs.

The sheet pack described in Patent Literature 4 exhibiting the effect of physically removing keratotic plugs can directly remove keratotic plugs and can achieve a significant reduction in pore clogging. However, in recent years, such a physical removal means causes anxiety of hurting the skin, and a technique of removing keratotic plugs with reduced pain and irritation of the skin is desired.

Accordingly, a novel technique capable of sufficiently exhibiting an excellent keratotic plug-removing effect without a burden, such as pain and irritation, on the skin has been desired to be developed.

Accordingly, the present inventors diligently studied to solve the above-mentioned problems and, as a result, found a method capable of more effectively removing keratotic plugs without causing excessive pain or feeling of irritation on the skin by using a composition containing a specific component, such as 2-amino-2-hydroxymethyl-1,3-propanediol, and accomplished the present invention.

According to the present invention, keratotic plugs can be effectively removed without a burden on the skin, and pore clogging and pore opening can be significantly suppressed to effectively avoid pore conspicuousness. In addition, it is possible to feel that the skin after removal of keratotic plugs is fine, soft, and bright and beautiful without darkening. It is also possible to increase the brightness of the skin and reduce skin dullness as well as enhance the penetration of an agent through the pores, leading to an expectation of an effect of increasing the action of the agent.

According to the present invention, not only keratotic plugs can be effectively removed, but also protein aggregation can be prevented. The invention is therefore useful as a skin cosmetic for cleansing pores and is also extremely useful as a protein aggregation suppresser or a skin external preparation for suppressing acne.

BRIEF DESCRIPTION OF DRAWING

FIG. 1 is a graph showing a relationship between the average amount of change in the average luminance of internally scattered light and the number of days in continuous use for 7 days, 14 days, and 21 days calculated in Example 2.

DETAILED DESCRIPTION OF THE INVENTION

The present invention will now be described in detail.
In the present specification, the term "keratotic plug" refers to a substance physiologically formed in pores of human skin and occluding the pores like a plug. The main components of the keratotic plug are a horny layer and proteins derived from a hair follicle. The keratotic plug is formed of a material in which these main components are mixed with proteins including proteins derived from acne bacteria or Staphylococcus and proteins derived from cellular organelles such as lysosomes and lipids including triglyceride, free fatty acids, and lipid peroxides.

The method for removing keratotic plugs of the present invention uses a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol (hereinafter, these components are also referred to as component (X)).

The composition may contain one or more selected from the group consisting of (X1) 2-amino-2-hydroxymethyl-1,3-propanediol, (X2) 2-amino-2-methyl-1-propanol, and (X3) 2-amino-2-methyl-1,3-propanediol as component (X), and these components may be contained singly or in combinations of two or more thereof.

By applying the composition comprising the component (X) to the skin, first the composition comprising the component (X) quickly penetrates into keratotic plugs to effectively elute lipids and the like, forming the keratotic plugs. In general, proteins such as the horny layer, readily aggregate and are hardly removed with a cleanser or the like. However, the composition containing the component (X) applied to the skin can suppress protein aggregation in parallel and can therefore effectively remove keratotic plugs, although the keratotic plugs contain proteins. Furthermore The component (X1), 2-amino-2-hydroxymethyl-1,3-propanediol, is specifically represented by the following formula (x1) and is also called "tris(hydroxymethyl)aminomethane" or "Tris".

(x1)

Such component (X1) has a molecular weight of 121.14, a melting point of 169° C. to 173° C., and a boiling point of 219° C. to 220° C. (10 mmHg). The component (X1) has a pKa of 8.03 at 25° C. indicating weak-basic properties and is readily dissolved in water.

The component (X2), 2-amino-2-methyl-1-propanol, is specifically represented by the following structural formula (x2) and is also simply called "AMP".

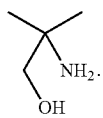

(x2)

Such component (X2) has a molecular weight of 89.14, a melting point of 30° C. to 31° C., and a boiling point of 165.5° C. (10 mmHg). The component (X2) has a pKa of 9.72 at 25° C. and is readily dissolved in water.

The component (X3), 2-amino-2-methyl-1,3-propanediol, is specifically represented by the following structural formula (x3) and is also simply called "AMPD".

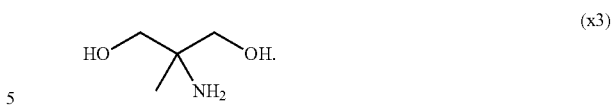

(x3)

Such component (X3) has a molecular weight of 105.14, a melting point of 107° C. to 112° C., and a boiling point of 151° C. (10 mmHg). The component (X3) has a pKa of 8.76 at 25° C. and is readily dissolved in water.

In particular, when one component is used as the component (X), the composition comprises preferably (X1) 2-amino-2-hydroxymethyl-1,3-propanediolas the component (X) from the viewpoint of improving the keratotic plug-removing effect. When two components are used as the component (X), the composition comprises preferably one selected from the group consisting of (X1) 2-amino-2-hydroxymethyl-1,3-propanediol and (X2) 2-amino-2-methyl-1-propanol, and (X3) 2-amino-2-methyl-1,3-propanediol, more preferably (X1) 2-amino-2-hydroxymethyl-1,3-propanediol and (X3) 2-amino-2-methyl-1,3-propanediol, from the same viewpoint as above.

When two or more components are used as the component (X), the mass ratio of the content of the component (X3) to the total content of the component (X1) and the component (X2), (X3)/((X1)+(X2)), is preferably 0.001 or more, more preferably 0.05 or more, further preferably 0.08 or more, further preferably 0.10 or more from the viewpoint of enhancing the keratotic plugs-removing effect while decreasing the burden on the skin. The mass ratio of the content of the component (X3) to the total content of the component (X1) and the component (X2), (X3)/((X1)+(X2)), is preferably, more preferably 50 or less, further preferably 20 or less, further preferably 10 or less from the viewpoint of sufficiently exhibiting the skin-softening effect while decreasing the burden on the skin. The mass ratio of the content of the component (X3) to the total content of the component (X1) and the component (X2), (X3)/((X1)+(X2)), is preferably from 0

The total content of the component (X) in the composition to be used is preferably 0.08 mass % or more, more preferably 0.10 mass % or more, further preferably 0.5 mass % or more, further preferably 0.8 mass % or more, further preferably 1.0 mass % or more, further preferably 2 mass % or more, further preferably 3 mass % or more, further preferably 4 mass % or more, further preferably 5 mass % or more from the viewpoint of a good combination of a keratotic plug-removing effect and a protein aggregation-suppressing effect. The total content of the component (X) in the composition to be used is preferably 35 mass % or less, more preferably 30 mass % or less, further preferably 25 mass % or less, further preferably 20 mass % or less, further preferably 15 mass % or less, further preferably 12 mass % or less, further preferably 11 mass % or less, further preferably 10 mass % or less from the viewpoint of a good combination of a keratotic plug-removing effect and a protein aggregation-suppressing effect. The total content of component (X) in the composition to be used is preferably from 0.08 to 35 mass %, more preferably from 0.10 to 30 mass %, further preferably from 0.5 to 25 mass %, further preferably from 0.8 to 20 mass %, further preferably from 1.0 to 20 mass %, further preferably from 2 to 15 mass %, further preferably from 3 to 12 mass %, further preferably from 4 to 11 mass %, further preferably from 5 to 10 mass %.

The composition used in the present invention may further contain (Y) a basic substance (hereinafter, also referred to as component (Y)) other than component (X), from the viewpoint of securing a high keratotic plug-removing effect and the viewpoint of further softening the skin together with the component (X).

The basic substance other than the component (X) is a component other than the component (X) and shows a basic property. Specifically, the basic substance is a compound showing a pH of 8 or more when it is dissolved in water of 25° C. to prepare an aqueous solution having a concentration of 1 mass %.

More specifically, examples of such component (Y) include one or more selected from the group consisting of linear or cyclic aliphatic amines such as monoethanolamine, triethanolamine, methylamine, ethylamine, trimethylamine, triethylamine, ethylenediamine, tetramethylethylenediamine, hexamethylenediamine, diethylenetriamine, triethylenetetramine, tetraethylenepentamine, pentaethylenehexamine, and morpholine; basic amino acids such as arginine and lysine; inorganic salts each composed of a strong base such as dipotassium hydrogen phosphate, disodium hydrogen phosphate, trisodium citrate, sodium bicarbonate, sodium acetate, lithium carbonate, sodium carbonate, potassium carbonate, potassium bicarbonate, or potassium acetate, and a weak acid such as carbonic acid, bicarbonic acid, acetic acid, phosphoric acid, citric acid, or a fatty acid; and aromatic amines such as aniline and pyridine.

In particular, the component (Y) includes preferably one or more selected from the group consisting of aliphatic amines and basic amino acids, more preferably one or more selected from the group consisting of arginine, monoethanolamine, triethanolamine, and morpholine, further preferably one or two selected from the group consisting of arginine and triethanolamine, further preferably arginine, from the viewpoint of improving the keratotic plug-removing effect and the skin-softening effect.

The total content of component (Y) in the composition to be used is preferably 0.01 mass % or more, more preferably 0.05 mass % or more, further preferably 0.10 mass % or more from the viewpoint of a good combination of a keratotic plug-removing effect and a skin-softening effect. The total content of the component (Y) in the composition to be used is preferably 15 mass % or less, more preferably 12 mass % or less, further preferably 10 mass % or less from the viewpoint of preventing an increase in irritation to the skin and improving the keratotic plug-removing effect. The total content of the component (Y) in the composition to be used is preferably from 0.01 to 15 mass %, more preferably from 0.05 to 12 mass %, further preferably from 0.10 to 10 mass %.

The total content of the component (X) and the component (Y) in the composition to be used is preferably 50 mass % or less, more preferably 32 mass % or less, more preferably 25 mass % or less, further preferably 20 mass % or less, further preferably 15 mass % or less, further preferably 12 mass % or less from the viewpoint of preventing an increase in irritation to the skin. The total content of the component (X) and the component (Y) in the composition to be used is preferably 0.09 mass % or more, more preferably 0.15 mass % or more, further preferably 0.50 mass % or more, further preferably 1.0 mass % or more, further preferably 2 mass % or more, further preferably 3 mass % or more, further preferably 5 mass % or more, further preferably higher than 5 mass % from the viewpoint of a good combination of a keratotic plug-removing effect and a protein aggregation-suppressing effect. The total content of the component (X) and the component (Y) in the composition to be used is preferably from 0.09 to 50 mass %, more preferably from 0.15 to 32 mass %, further preferably from 0.50 to 25 mass %, further preferably from 1.0 to 20 mass %, further preferably from 2 to 15 mass %, further preferably from 3 to 12 mass %, further preferably from 5 to 12 mass %, further preferably higher than 5 mass % and 12 mass % or less.

In the composition used in the present invention, the mass ratio of the content of the component (X) to the content of the component (Y), (X)/(Y), is preferably 0.001 or more, more preferably 0.005 or more, further preferably 0.008 or more, further preferably 0.010 or more from the viewpoint of enhancing the keratotic plug-removing effect while suppressing the burden on the skin. In the composition used in the present invention, the mass ratio of the content of the component (X) to the content of the component (Y), (X)/(Y), is preferably 200 or less, more preferably 150 or less, further preferably 120 or less, further preferably 100 or less from the viewpoint of sufficiently exhibiting the skin-softening effect while suppressing the burden on the skin. In the composition used in the present invention, the mass ratio of the content of the component (X) to the content of the component (Y), (X)/(Y), is from preferably 0.001 to 200, more preferably from 0.005 to 150, further preferably from 0.008 to 120, further preferably from 0.01 to 100.

The component (X) is preferably present in a free form, instead of a salt form, in the composition from the viewpoint of improving the detergency against keratotic plugs. That is, preferably, the component (X) does not form a salt such as a fatty acid salt, together with an acidic component such as an unneutralized fatty acid and is at least partially present in a free form so that component (X) is independently present in the composition. The mass ratio of the content of the component (X) present in a free form to the content of the whole component (X) in the composition to be used, (content of free-form component (X))/(content of component (X)), is preferably 0.6 or more, more preferably 0.8 or more, further preferably 0.9 or more, further preferably 1.0, from the viewpoint mentioned above.

Similarly, the component (Y) in the composition is also preferably present in a free form, instead of a salt form, from the viewpoint of improving the detergency against keratotic plugs and the skin-softening properties. For example, preferably, the component (Y) does not form a salt such as a fatty acid salt, with an acidic component such as an unneutralized fatty acid and is at least partially present in a free form so that the component (Y) is independently present in the composition. The mass ratio of the content of the component (Y) present in a free form to the content of the component (Y) in the composition to be used, (content of free-form component (Y))/(content of component (Y)), is preferably 0.6 or more, more preferably 0.8 or more, further preferably 0.9 or more, further preferably 1.0, from the viewpoint mentioned above.

The composition used in the present invention may further contain (A) an anionic surfactant, in addition to the above-mentioned components, from the viewpoint of improving the foaming property. From the viewpoint of further enhancing the keratotic plug-removing effect, the composition preferably contains (A1) an anionic surfactant having a carboxylic acid group and/or (A2) an anionic surfactant having a sulfonic acid group or sulfate group as the anionic surfactant (A).

The term "carboxylic acid group" means encompassment of a carboxylate residue. Such anionic surfactants having carboxylic acid groups as the component (A1) include preferably one or more selected from the group consisting of fatty acids or salts thereof, ether carboxylic acids or salts thereof, and N-acylamino acid salts, more preferably ether carboxylic acids or salts thereof.

The fatty acids or salts thereof that can be used as the component (A1) is, from the viewpoint of exhibiting a good foaming property and further enhancing the keratotic plug-removing effect, preferably a fatty acid or a salt thereof having a linear or branched alkyl group having 10 to 22 carbon atoms, more preferably a fatty acid or a salt thereof having a linear or branched alkyl group having 10 to 18 carbon atoms, further preferably a fatty acid or a salt thereof having a linear alkyl group having 12 to 16 carbon atoms, further preferably a fatty acid or a salt thereof having a linear alkyl group having 12 to 14 carbon atoms. Specifically, examples thereof include one or more selected from the group consisting of lauric acid, myristic acid, palmitic acid, stearic acid, behenic acid, and salts thereof. In particular, from the same viewpoint as above, the component (A1) includes preferably one or more selected from the group consisting of laurates, myristates, and palmitates, more preferably one or two selected from the group consisting of laurates and myristates.

The salt constituting the fatty acid salt as the component (A1) includes preferably one or more selected from the group consisting of alkali metals and ammonium, more preferably one or more selected from the group consisting of alkali metals, further preferably sodium salts.

The composition to be used may contain, as component (A1), for example, a fatty acid salt formed from an unneutralized fatty acid and a neutralizer. The neutralization rate of the fatty acid is preferably from 50% to 100%, more preferably from 70% to 100%, further preferably from 90% to 100%, further preferably 100%, from the viewpoint of improving the volume of foam and the foaming property. The neutralizer is specifically preferably one or two selected from the group consisting of potassium hydroxide and sodium hydroxide.

Examples of the ether carboxylic acid or salt thereof that can be used as the component (A1) include an ether carboxylic acid or a salt thereof represented by the following Formula (1):

$$R^1O(CH_2CH_2O)_mCH_2COOM^1 \quad (1)$$

wherein $R^1$ represents an alkyl or alkenyl group having 10 to 22 carbon atoms; m represents a number of 0.5 to 10 on average; and $M^1$ represents a hydrogen atom, an alkali metal, an alkaline earth metal, ammonium, or an organic ammonium.

In Formula (1), $R^1$ is preferably an alkyl group having 12 to 16 carbon atoms, more preferably an alkyl group having 12 to 14 carbon atoms from the viewpoint of exhibiting a good foaming property and further enhancing the keratotic plug-removing effect. From the same viewpoint as above, the average addition mole number m of ethylene oxide is preferably from 2 to 5.

Examples of $M^1$ includes a hydrogen atom; an alkali metal such as sodium or potassium; an alkaline earth metal such as calcium or magnesium; ammonium; alkanolamine-derived ammonium such as monoethanolamine, diethanolamine, or triethanolamine; and basic amino acid-derived ammonium such as arginine or lysine. Among them, from the same viewpoint as above, $M^1$ preferably represents one or more selected from the group consisting of sodium, potassium, triethanolamine, and arginine, more preferably one or two selected from the group consisting of sodium and potassium.

From the same viewpoint as above, specifically, the ether carboxylic acid or salt thereof includes preferably one or more selected from the group consisting of polyoxyethylene lauryl ether carboxylate, polyoxyethylene myristyl ether carboxylate, and polyoxyethylene palmityl ether carboxylate; preferably one or two selected from the group consisting of polyoxyethylene lauryl ether carboxylate and polyoxyethylene myristyl ether carboxylate; and further preferably polyoxyethylene lauryl ether carboxylate.

Commercially available examples of the ether carboxylic acid or salt thereof include AKYPO RLM 45CA (manufactured by Kao Corporation) and AKYPO LM 26C (manufactured by Kao Corporation).

The composition to be used may contain, as the component (A1), for example, an ether carboxylate formed from an unneutralized ether carboxylic acid and a neutralizer. The neutralization rate of the ether carboxylic acid is preferably from 50% to 100%, more preferably from 70% to 100%, further preferably from 90% to 100%, further preferably 100% from the viewpoint of improving the volume of foam and the foaming property. The neutralizer is specifically preferably one or two selected from the group consisting of potassium hydroxide and sodium hydroxide.

Examples of the acylamino acid salt that can be used as the component (A1) include N-acylamino acids or salts thereof. The acyl group of the N-acylamino acid or salt thereof is preferably derived from a saturated or unsaturated, linear or branched fatty acid having 4 to 30 carbon atoms, more preferably derived from a saturated or unsaturated, linear or branched fatty acid having 6 to 26 carbon atoms, further preferably derived from a saturated or unsaturated, linear or branched fatty acid having 8 to 24 carbon atoms, from the viewpoint of exhibiting a good foaming property and further enhancing the keratotic plug-removing effect. Examples of such a fatty acid include caprylic acid, capric acid, lauric acid, myristic acid, palmitic acid, stearic acid, and oleic acid. Among these fatty acids, from the same viewpoint as above, one or more selected from the group consisting of lauric acid, myristic acid, palmitic acid, and oleic acid are preferable; and lauric acid is more preferable. The acyl group of the N-acylamino acid may be derived from a mixture of the above-mentioned fatty acids, for example, one obtained from coconut oil, palm kernel oil or the like, as a raw material. In particular, one obtained from coconut oil fatty acids or palm kernel fatty acids as a raw material is preferable; and one obtained from coconut oil fatty acids as a raw material is more preferable.

The amino acid portion of the N-acylamino acid or salt thereof is preferably a neutral amino acid selected from the group consisting of glycine and alanine or an acidic amino acid selected from the group consisting of glutamic acid and aspartic acid, more preferably an acidic amino acid, further preferably glutamic acid, from the viewpoint of exhibiting a good foaming property and further enhancing the keratotic plug-removing effect. The amino acid portion may be the D-form, the L-form, or a mixture of D- and L-forms and is preferably the L-form.

The N-acylamino acids or salts thereof may be used singly or in combinations of two or more thereof. In particular, from the viewpoint of a good foaming property and improving the smoothness of the skin, the N-acylamino acids or salt thereof include preferably at least one selected from the group consisting of N-lauroyl glutamic acid, N-myristoyl glutamic acid, N-cocoyl glutamic acid, N-palm fatty acid glutamic acid, N-lauroyl aspartic acid, N-cocoyl glycine, N-cocoyl alanine, and salts thereof; more preferably at least one selected from the group consisting of N-lauroyl glutamic acid, N-myristoyl glutamic acid, N-cocoyl glutamic acid, N-palm fatty acid glutamic acid, N-lauroyl aspartic acid, N-cocoyl glycine, and salts thereof; further preferably at least one selected from the group consisting of N-lauroyl glutamic acid, N-myristoyl glutamic acid, N-cocoyl glutamic acid, N-lauroyl aspartic acid, and salts thereof; further preferably at least one selected from the group consisting of N-cocoyl glutamic acid, N-lauroyl aspartic acid, and salts thereof; further preferably N-cocoyl glutamic acid or a salt thereof.

The salt of the N-acylamino acid or salt thereof may be preferably at least one salt selected from the group consisting of an alkali metal salt, a triethanolamine salt, and an arginine salt, more preferably at least one salt selected from the group consisting of a sodium salt, a potassium salt, and a triethanolamine salt, further preferably at least one salt selected from the group consisting of a sodium salt and a potassium salt, further preferably a sodium salt, from the viewpoint of reducing irritation to the skin and easiness of acquisition.

The N-acylamino acid used is preferably prepared by neutralization with a base. The neutralization rate of the N-acylamino acid preferably from 80% to 100%, more preferably from 90% to 100%, further preferably 1001 from the viewpoint of improving the volume of foam and the foaming property. The neutralizer is specifically preferably one or two selected from the group consisting of potassium hydroxide and sodium hydroxide.

The content of the component (A1) in the composition to be used is preferably 0.01 mass % or more, more preferably 0.05 mass % or more, further preferably 0.10 mass % or more, further preferably 0.3 mass % or more from the viewpoint of a good foaming property and exhibiting a keratotic plug-removing effect. The content of the component (A1) in the composition to be used is preferably 5 mass % or less, more preferably 3 mass % or less, further preferably 2.0 mass % or less, further preferably 1.5 mass % or less, further preferably 1.0 mass % or less from the viewpoint of preventing an increase in the burden on the skin and exhibiting an excellent keratotic plug-removing effect. The content of the component (A1) in the composition to be used is preferably from 0.01 to 5 mass %, more preferably from 0.05 to 3 mass %, further preferably from 0.05 to 2.0 mass %, further preferably from 0.10 to 1.5 mass %, further preferably from 0.3 to 1.0 mass %.

The "content" of the component (A1) refers to the amount in terms of a fatty acid when the fatty acid or a salt thereof mentioned above is used as the component (A) and refers to the amount in terms of an acid when the ether carboxylic acid or a salt thereof or the N-acylamino acid or a salt thereof is used.

In the composition used in the present invention, the mass ratio of the content of the component (X) to the content of the component (A1), (X)/(A1), is preferably 0.1 or more, more preferably 0.5 or more, further preferably 1.0 or more from the viewpoint of exhibiting an excellent keratotic plug-removing effect. The mass ratio of the content of the component (X) to the content of the component (A1), (X)/(A1), is preferably 100 or less, more preferably 80 or less, further preferably 70 or less from the viewpoint of exhibiting an excellent keratotic plug-removing effect and maintaining a good foaming property. The mass ratio of the content of the component (X) to the content of the component (A1), (X)/(A1), is preferably from 0.1 to 100, more preferably from 0.5 to 80, further preferably from 1.0 to 70.

In particular, when component (X) is either component (X1) or (X2), the mass ratio of the content of component (X) to the content of component (A1), (X)/(A1), is further preferably 2 or more, further preferably 5 or more, and further preferably 8 or more and further preferably 60 or less, further preferably 50 or less, further preferably 40 or less, further preferably 30 or less, and further preferably 20 or less, from the viewpoint of exhibiting an excellent keratotic plug-removing effect and maintaining good foaming properties. The mass ratio of the content of component (X) to the content of component (A1), (X)/(A1), is further preferably 2 to 60, further preferably 2 to 50, further preferably 5 to 40, further preferably 8 to 30, and further preferably 8 to 20.

In particular, when component (X) is component (X3) only, the mass ratio of the content of component (X) to the content of component (A1), (X)/(A1), is further preferably 2 or more, further preferably 5 or more, further preferably 8 or more, further preferably 15 or more, further preferably 30 or more, and further preferably 40 or more and further preferably 68 or less, further preferably 65 or less, further preferably 62 or less, and further preferably 60 or less, from the viewpoint of exhibiting an excellent keratotic plug-removing effect and maintaining a good foaming property. The mass ratio of the content of component (X) to the content of component (A1), (X)/(A1), is further preferably 2 to 68, further preferably 5 to 65, further preferably 8 to 62, further preferably 15 to 60, further preferably 30 to 60, and further preferably 40 to 60.

The term "sulfonic acid group or sulfate group" of the anionic surfactant having a sulfonic acid group or sulfate group as the component (A2) means including a sulfonate residue or sulfate residue. Examples of such an anionic surfactant having a sulfonic acid group or sulfate group as the component (A2) include one or more selected from the group consisting of alkylbenzene sulfonic acids or salts thereof, alkanesulfonic acids or salts thereof, alkenylsulfonic acids or salts thereof, alkylsulfonic acids or salts thereof, acylisethionic acids or salts thereof, alkyl sulfates or salts thereof, alkyl ether sulfates or salts thereof, alkyl sulfosuccinic acids or salts thereof, sulfofatty acid methyl esters or salts thereof, fatty acid alkanolamide sulfates or salts thereof, and monoacylglycerol sulfate or salts thereof. The salt constituting the component (A2) is preferably an inorganic salt selected from the group consisting of a sodium salt, a potassium salt, a lithium salt, a magnesium salt, and an ammonium salt; or an organic amine salt selected from the group consisting of a monoethanolamine salt, a diethanolamine salt, and a triethanolamine salt.

Among them, from the viewpoint of maintaining a good foaming property while exhibiting an excellent keratotic plug-removing effect, the component (A2) includes preferably one or more selected from the group consisting of alkylbenzene sulfonic acids or salts thereof, acylisethionic acids or salts thereof, alkyl sulfates or salts thereof, alkyl ether sulfates or salts thereof, alkenylsulfonic acids or salts thereof, and alkylsulfonic acids or salts thereof; more preferably one or more selected from the group consisting of alkyl sulfates or salts thereof, alkyl ether sulfates or salts thereof, alkenylsulfonic acids or salts thereof, and alkylsulfonic acids or salts thereof; further preferably one or more selected from the group consisting of alkyl sulfate salts, alkyl ether sulfate salts, alkenylsulfonic acid salts, and alkylsulfonic acid salts.

Examples of the alkyl sulfate salt that can be used as the component (A2) include alkyl sulfate salts represented by the following Formula (2):

$$R^2OSO_3M^2 \qquad (2)$$

wherein R² represents an aliphatic hydrocarbon group having 8 to 22 carbon atoms; and M² represents a cation selected from the group consisting of an alkali metal, an alkaline earth metal, ammonium, alkyl ammonium, alkanol ammonium, and glucammonium.

In Formula (2), R² preferably represents an aliphatic hydrocarbon group having 8 to 18 carbon atoms, more preferably an aliphatic hydrocarbon group having 8 to 16 carbon atoms, further preferably an aliphatic hydrocarbon group having 10 to 16 carbon atoms from the viewpoint of maintaining a good foaming property while exhibiting an excellent keratotic plug-removing effect. Furthermore, R² preferably represents an alkyl or alkenyl group having 8 to 16 carbon atoms, more preferably an alkyl or alkenyl group having 10 to 16 carbon atoms, further preferably an alkyl or alkenyl group having 10 to 14 carbon atoms.

M² preferably represents an alkali metal or ammonium, more preferably an alkali metal, further preferably a sodium salt from the same viewpoint as above.

Specifically, examples of the alkyl sulfate salt include sodium lauryl sulfate, triethanolamine lauryl sulfate, ammonium lauryl sulfate, sodium myristyl sulfate, sodium cetyl sulfate, sodium stearyl sulfate, sodium oleyl sulfate, and triethanolamine oleyl sulfate. Among them, the alkyl sulfate salt preferably includes one or more selected from the group consisting of sodium lauryl sulfate, triethanolamine lauryl sulfate, and ammonium lauryl sulfate. These compounds may be used singly or in combinations of two or more thereof.

Commercially available examples of the alkyl sulfate salt include Emal 0S (manufactured by Kao Corporation, sodium lauryl sulfate), Emal 10PT (manufactured by Kao Corporation, sodium lauryl sulfate), Emal TD (manufactured by Kao Corporation, triethanolamine lauryl sulfate), and Emal AD-25R (manufactured by Kao Corporation, ammonium lauryl sulfate).

Examples of the alkyl ether sulfate salt that can be used as the component (A2) include alkyl ether sulfate salts represented by the following Formula (3):

$$R^3O(CH_2CH_2O)_nSO_3M^3 \quad (3)$$

wherein R³ represents an aliphatic hydrocarbon group having 8 to 22 carbon atoms; M³ represents a cation selected from the group consisting of an alkali metal, alkaline earth metal, ammonium, alkyl ammonium, alkanol ammonium, and glucammonium; and n represents an average addition mole number and is 0.5 to 20.

In Formula (3), R³ preferably represents an aliphatic hydrocarbon group having 8 to 18 carbon atoms, more preferably an aliphatic hydrocarbon group having 8 to 16 carbon atoms, further preferably an aliphatic hydrocarbon group having 10 to 16 carbon atoms from the viewpoint of maintaining a good foaming property while exhibiting an excellent keratotic plug-removing effect. Furthermore, R³ preferably represents an alkyl or alkenyl group having 8 to 16 carbon atoms, more preferably an alkyl or alkenyl group having 10 to 16 carbon atoms, further preferably an alkyl or alkenyl group having 10 to 14 carbon atoms.

n represents preferably 0.5 or more; and preferably 12 or less, more preferably 5 or less, further preferably 4 or less, further preferably 2 or less, from the same viewpoint as above. Specifically, the range of n is preferably from 0.5 to 12, more preferably from 0.5 to 5, further preferably from 0.5 to 4, further preferably from 0.5 to 2.

M³ preferably represents an alkali metal or ammonium, more preferably an alkali metal, further preferably a sodium salt, from the same viewpoint as above.

Specifically, examples of the alkyl ether sulfate salt include one or more selected from the group consisting of sodium polyoxyethylene (1) lauryl ether sulfate, ammonium polyoxyethylene (1) lauryl ether sulfate, sodium polyoxyethylene (1) myristyl ether sulfate, sodium polyoxyethylene (2) lauryl ether sulfate, and sodium polyoxyethylene (2) myristyl ether sulfate. Among them, the alkyl ether sulfate salt preferably includes one or more selected from the group consisting of sodium polyoxyethylene (1) lauryl ether sulfate, polyoxyethylene (1) ammonium lauryl ether sulfate, and sodium polyoxyethylene (2) lauryl ether sulfate. In the present specification, the numbers in parentheses shown in these compounds each mean the average addition mole number of ethylene oxide.

Commercially available examples of the alkyl ether sulfate salt include Emal 125HP (manufactured by Kao Corporation, sodium polyoxyethylene (1) lauryl ether sulfate), Emal 125A (manufactured by Kao Corporation, ammonium polyoxyethylene (1) lauryl ether sulfate), and Emal 227 (manufactured by Kao Corporation, sodium polyoxyethylene (2) lauryl ether sulfate).

The alkenylsulfonic acid or a salt thereof that can be used as the component (A2) is preferably an alkenylsulfonic acid or a salt thereof which is a linear hydrocarbon having 12 to 22 carbon atoms and a double bond, more preferably a linear hydrocarbon having 12 to 18 carbon atoms and a double bond, and formed by bonding a sulfo group to any of the carbon atoms other than the terminal carbon atoms. The alkenylsulfonic acid or salt thereof is further preferably an alkenylsulfonic acid or a salt thereof which is a linear hydrocarbon having 12 to 18 carbon atoms and a double bond, in which the double bond is present at 3- or higher internal position of the linear hydrocarbon in 70 mass % or more thereof and which is formed by bonding a sulfo group to any of the carbon atoms other than the terminal carbon atoms.

These alkenylsulfonic acid having 12 to 22 carbon atoms or salts thereof may be used singly or in combinations of two or more thereof and are preferably used in combination of two or more thereof according to the purpose of use from the viewpoint of the foaming property and being capable of controlling the foam quality. Furthermore, an alkenylsulfonic acid having 16 carbon atoms or a salt thereof and an alkenylsulfonic acid having 18 carbon atoms or a salt thereof are preferable from the viewpoint of the foaming property and foam quality. In addition, the alkenylsulfonic acid having 16 carbon atoms or a salt thereof and the alkenylsulfonic acid having 18 carbon atoms or a salt thereof are preferably used as a mixture. In such a case, the mass ratio of the alkenylsulfonic acid having 16 carbon atoms or salt thereof to the alkenylsulfonic acid having 18 carbon atoms or salt thereof is preferably from 1/9 to 9/1, more preferably from 2/8 to 8/2, and further preferably from 5/5 to 2/8. The use of the mixture can enhance the feeling during rinsing.

Examples of the salt constituting the alkenylsulfonic acid salt include alkali metals such as sodium and potassium; alkaline earth metals such as calcium and magnesium; ammonium; and salts constituted of organic ammonium derived from monoethanolamine, diethanolamine, triethanolamine, or the like. Among them, alkali metal salts and ammonium salts are preferable from the viewpoint of market availability.

The alkylsulfonic acid or salt thereof that can be used as component (A2) is preferably a hydroxyalkylsulfonic acid having 12 to 22 carbon atoms or a salt thereof, more preferably a hydroxyalkylsulfonic acid having 12 to 22 carbon atoms or a salt thereof and formed by bonding a sulfo group to any of the carbon atoms other than the terminal carbon atoms, further preferably a hydroxyalkylsulfonic acid having 12 to 18 carbon atoms or a salt thereof and formed by bonding a sulfo group to a carbon atom other than the terminal carbon atoms. Further preferably, the hydroxyalkylsulfonic acid or salt thereof is preferably a hydroxyalkylsulfonic acid which is a linear hydrocarbon having 12 to 18 carbon atoms and formed by each bonding a hydroxyl group to any of the carbon atoms other than the terminal carbon atoms and a sulfo group to any of the carbon atoms other than the terminal carbon atoms.

These hydroxyalkylsulfonic acids having 12 to 22 carbon atoms or salts thereof may be used singly or in combinations of two or more thereof and are preferably used in combination of two or more thereof according to the purpose of use from the viewpoint of the foaming property and being capable of controlling the foam quality. Furthermore, a hydroxyalkylsulfonic acid having 16 carbon atoms or a salt thereof and a hydroxyalkylsulfonic acid having 18 carbon atoms or a salt thereof are preferable from the viewpoint of the foaming property and foam quality. In addition, the hydroxyalkylsulfonic acid having 16 carbon atoms or salt thereof and the hydroxyalkylsulfonic acid having 18 carbon atoms or salt thereof are preferably used as a mixture. In such a case, the mass ratio of the hydroxyalkylsulfonic acid having 16 carbon atoms or salt thereof to the hydroxyalkylsulfonic acid having 18 carbon atoms or salt thereof, (hydroxyalkylsulfonic acid having 16 carbon atoms or salt thereof /hydroxyalkylsulfonic acid having 18 carbon atoms or salt thereof), is preferably from 9/1 to 1/9, more preferably from 8/2 to 2/8, further preferably from 5/5 to 2/8. The use of the mixture can enhance the feeling during rinsing.

Examples of the salt constituting the alkylsulfonic acid salt include alkali metals, such as sodium and potassium; alkaline earth metals, such as calcium and magnesium; ammonium; and salts constituted of organic ammonium derived from monoethanolamine, diethanolamine, triethanolamine, or the like. Among them, alkali metal salts and ammonium salts are preferable from the viewpoint of market availability.

The component (A2) may be an alkenylsulfonic acid or a salt thereof or an alkylsulfonic acid or a salt thereof or may be a mixture of an alkenylsulfonic acid or a salt thereof and an alkylsulfonic acid or a salt thereof. In the mixture, the mass ratio of the alkenylsulfonic acid or salt thereof to the alkylsulfonic acid or salt thereof, (alkenylsulfonic acid or salt thereof /alkylsulfonic acid or salt thereof), is preferably from 5/95 to 50/50, more preferably from 10/90 to 30/70.

The alkenylsulfonic acid or salt thereof and the alkylsulfonic acid or salt thereof can be produced by, for example, the method described in JP-A-2015-28123.

The content of the component (A2) in the composition used in the present invention is preferably 0.01 mass % or more, more preferably 0.03 mass % or more, further preferably 0.05 mass % or more, further preferably 0.10 mass % or more; and preferably 20 mass % or less, more preferably 18 mass % or less, and preferably 15 mass % or less, from the viewpoint of exhibiting a good keratotic plug-removing effect and foaming property. The content of component (A2) in the composition to be used is preferably from 0.01 to 20 mass %, more preferably from 0.03 to 18 mass %, further preferably from 0.05 to 18 mass %, further preferably from 0.10 to 15 mass %.

In particular, when component (X) is either component (X1) or (X2), the content of the component (A2) in the composition used in the present invention is further preferably 0.2 mass % or more, further preferably 0.3 mass % or more, further preferably 0.5 mass % or more from the viewpoint of exhibiting a good keratotic plug-removing effect and foaming properties; and is further preferably 12 mass % or less, further preferably 10 mass % or less, further preferably 8 mass % or less, further preferably 5 mass % or less, further preferably 4 mass % or less, further preferably 3 mass % or less. The content of component (A2) in the composition to be used is further preferably from 0.2 to 12 mass %, further preferably from 0.2 to 10 mass %, further preferably from 0.2 to 8 mass %, further preferably from 0.3 to 5 mass %, further preferably from 0.3 to 4 mass %, further preferably from 0.5 to 3 mass %.

In particular, when the component (X) is the component (X3) only, the content of the component (A2) in the composition used in the present invention is preferably 0.2 mass % or more, more preferably 0.3 mass % or more, further preferably 0.5 mass % or more, further preferably 1.0 mass % or more, further preferably 1.5 mass % or more, further preferably 2.0 mass % or more from the viewpoint of exhibiting a good keratotic plug-removing effect and foaming property; and is preferably 14 mass % or less, more preferably 13 mass % or less, further preferably 12 mass % or less, further preferably 11 mass % or less, further preferably 10 mass % or less. The content of the component (A2) in the composition to be used is preferably from 0.2 to 14 mass %, more preferably from 0.3 to 14 mass %, further preferably from 0.5 to 13 mass %, further preferably from 1.0 to 12 mass %, further preferably from 1.5 to 11 mass %, further preferably from 2.0 to 10 mass %.

In the composition of the present invention, the mass ratio of the content of the component (X) to the content of the component (A2), (X)/(A2), is preferably 0.005 or more, more preferably 0.01 or more, further preferably 0.10 or more, further preferably 0.20 or more, further preferably 0.25 or more, further preferably 0.3 or more, further preferably 0.5 or more from the viewpoint of maintaining a good foaming property. The mass ratio is preferably 100 or less, more preferably 60 or less, further preferably 50 or less, further preferably 40 or less, further preferably 30 or less, further preferably 20 or less, further preferably 15 or less, further preferably 14 or less, further preferably 12.5 or less from the viewpoint of preventing an increase in the burden on the skin and exhibiting an excellent keratotic plug-removing effect. The mass ratio of the content of the component (X) to the content of the component (A2), (X)/(A2), is preferably from 0.005 to 100, more preferably from 0.01 to 60, further preferably from 0.10 to 50, further preferably from 0.20 to 40, further preferably from 0.20 to 30, further preferably from 0.20 to 20, further preferably from 0.25 to 15, further preferably from 0.3 to 14, further preferably from 0.50 to 12.5.

The composition used in the present invention may contain an anionic surfactant other than the components (A1) and (A2). Examples of the anionic surfactant other than the components (A1) and (A2) include a phosphate surfactant, and specific examples thereof include alkyl phosphate salts, polyoxyethylene alkyl ether phosphate salts, alkylaryl ether phosphate salts, and fatty acid amide ether phosphoric acids.

Although the content of the anionic surfactant other than the components (A1) and (A2) varies depending on the dosage form of the composition to be used, the content in the composition is preferably 0.01 mass % or more, more preferably 0.05 mass % or more, further preferably 0.10 mass % or more; and preferably 10 mass % or less, more preferably 5 mass % or less, further preferably 1.0 mass % or less, further preferably 0.5 mass % or less from the viewpoint of maintaining a good foaming property while exhibiting an excellent keratotic plug-removing effect.

The total content of the component (A) in the composition to be used is preferably 0.01 mass % or more, more preferably 0.02 mass % or more, further preferably 0.05 mass % or more, further preferably 0.1 mass % or more, further preferably 0.3 mass % or more, further preferably 0.5 mass % or more from the viewpoint of exhibiting a good keratotic plug-removing effect and foaming property. The content of the component (A) in the composition to be used is preferably 30 mass % or less, more preferably 20 mass % or less, further preferably 15 mass % or less, further preferably 12 mass % or less, further preferably 10 mass % or less, further preferably 8 mass % or less, further preferably 4 mass % or less from the viewpoint of preventing an increase in the burden on the skin. The content of the component (A) in the composition to be used is preferably from 0.01 to 30 mass %, more preferably from 0.02 to 20 mass %, further preferably from 0.05 to 15 mass %, further preferably from 0.1 to 12 mass %, further preferably from 0.1 to 10 mass %, further preferably from 0.3 to 8 mass %, further preferably from 0.5 to 4 mass %.

The composition of the present invention preferably further contains (B) a nonionic surfactant from the viewpoint of exhibiting good sebum cleansing ability and makeup removability and further enhancing the keratotic plug-removing effect.

The component (B) preferably includes (B1) a nonionic surfactant having an HLB of 11 or more from the viewpoint of enhancing the sebum cleansing ability and the keratotic plug-removing effect. The HLB of such component (B1) is 11 or more, and is preferably 12 or more, more preferably 13 or more; and preferably 20 or less, more preferably 19 or less, further preferably 18 or less. The component (B1) has an HLB of 11 or more, preferably from 11 to 20, more preferably from 12 to 19, further preferably from 13 to 18.

Herein, the HLB (Hydrophilic-Lypophilic Balance) of the nonionic surfactant indicates the molecular weight of the hydrophilic group moiety accounting for the total molecular weight of the nonionic surfactant and is determined by the following equation of Griffin:

HLB=20×(molecular weight of hydrophilic group moiety in surfactant molecule/molecular weight of surfactant).

Examples of the nonionic surfactant as the component (B1) include polyglycerol fatty acid esters, polyethylene glycol fatty acid esters, polyoxyethylene glycerol fatty acid esters, polyoxyethylene polyoxypropylene glycol, polyoxyethylene sorbitan fatty acid esters, polyoxyethylene sorbitol fatty acid esters, polyoxyethylene castor oils, polyoxyethylene hydrogenated castor oils, polyoxyethylene hydrogenated castor oil fatty acid esters, polyoxyethylene alkyl ethers, polyoxyethylene alkyl ether fatty acid esters, sucrose fatty acid esters, alkyl polyglucosides, and (poly)alkyl glyceryl ethers.

In particular, from the viewpoint of improving sebum cleansing ability and rinsing performance, the component (B1) includes preferably one or more selected from the group consisting of polyglycerol fatty acid esters, polyethylene glycol fatty acid esters, polyoxyethylene glycerol fatty acid esters, polyoxyethylene sorbitan fatty acid esters, polyoxyethylene hydrogenated castor oil fatty acid esters, polyoxyethylene alkyl ethers, and alkyl polyglucosides, more preferably one or more selected from the group consisting of polyethylene glycol fatty acid esters, polyoxyethylene alkyl ethers, polyoxyethylene sorbitan fatty acid esters, and alkyl polyglucosides.

The commercial product of the polyoxyethylene sorbitan fatty acid ester is preferably, for example, polyoxyethylene (6) lauric acid sorbitan (Rheodol TW-L106 (HLB: 13.3), manufactured by Kao Corporation).

The commercial product of the polyethylene glycol fatty acid ester is preferably, for example, polyethylene glycol monolaurate (12EO) (Emanon 112 (HLB: 13.7), manufactured by Kao Corporation).

The commercial product of the polyoxyethylene alkyl ether is preferably, for example, polyoxyethylene (21) lauryl ether (Emulgen 121-G (HLB: 16.6), manufactured by Kao Corporation), polyoxyethylene (20) 2-hexyldecyl ether (Emulgen 1620G (HLB: 14), manufactured by Kao Corporation), polyoxyethylene (16) lauryl ether (Emulgen 116 (HLB: 15.8), manufactured by Kao Corporation), polyoxyethylene (9) lauryl ether (Emulgen 109P (HLB: 13.6), manufactured by Kao Corporation), polyoxyethylene (20) octyldodecyl ether (Emulgen 2020G (HLB: 13.3), manufactured by Kao Corporation), or polyoxyethylene (25) octyldodecyl ether (Emulgen 2025G (HLB: 14.1), manufactured by Kao Corporation).

The commercial product of the alkyl polyglucoside is preferably, for example, decyl glucoside (Mydol 10 (HLB: 15.7), manufactured by Kao Corporation) or lauryl glucoside (Mydol 12 (HLB: 17), manufactured by Kao Corporation).

The component (B) preferably contains (B2) a nonionic surfactant having an HLB of less than 11 from the viewpoint of exhibiting better makeup removability. The HLB of the component (B2) is less than 11, preferably 10 or less, more preferably 9 or less; and preferably 4 or more, more preferably HLB 5 or more, further preferably HLB 6 or more. The HLB of the component (B2) is less than 11, is preferably from 4 to 10, more preferably from 5 to 10, further preferably from 6 to 9.

Examples of the nonionic surfactant as the component (B2) include polyethylene glycol surfactants, i.e., ethylene glycol fatty acid esters such as ethylene glycol monostearate, polyethylene glycol fatty acid esters such as polyethylene glycol (2) monostearate, polyethylene glycol alkyl ethers such as polyethylene glycol (5) decyl pentadecyl ether, and polyethylene glycol hydrogenated castor oils such as polyethylene glycol (5) hydrogenated castor oil monoisolaurate; propylene glycol surfactants, i.e., propylene glycol fatty acid esters, polypropylene glycol fatty acid esters, propylene glycol alkyl ethers, polypropylene glycol alkyl ethers, and ethylene oxide derivatives of propylene glycol alkyl ether; glycerol fatty acid esters such as glycerol monoisostearate; glycerol alkyl ethers such as glycerol monoisostearyl ether; sorbitan fatty acid esters such as sorbitan monostearate; and polyglycerol fatty acid esters such as polyglyceryl monoisostearate.

In particular, the component (B2) preferably includes one or more selected from the group consisting of polyoxyethylene alkyl ethers and polyglycerol fatty acid esters.

The commercial product of the polyoxyethylene alkyl ether is preferably, for example, polyoxyethylene (2) lauryl ether (Emulgen 102 (HLB: 6.4), manufactured by Kao Corporation), polyoxyethylene (3) lauryl ether (Emulgen 103 (HLB: 8.3), manufactured by Kao Corporation), or polyoxyethylene (5) lauryl ether (Emulgen 105 (HLB: 10), manufactured by Kao Corporation).

The commercial product of the polyglycerol fatty acid ester is preferably, for example, polyglyceryl isostearate (Cosmol 41V (HLB: 8), manufactured by The Nisshin OilliO Group, Ltd.).

In the composition of the present invention, the mass ratio of the content of the nonionic surfactant having an HLB of 11 or more as the component (B1) to the content of the nonionic surfactant having an HLB of less than 11 as the component (B2), (B1)/(B2), is preferably 0.1 or more, more preferably 0.6 or more, further preferably 0.8 or more, further preferably 1.5 or more, further preferably 2.5 or more, further preferably 5 or more; and preferably 25 or less, more preferably 20 or less, further preferably 16 or less, further preferably 14 or less, further preferably 12 or less from the viewpoint of exhibiting good sebum cleansing ability and makeup removability. The mass ratio of the content of the nonionic surfactant having an HLB of 11 or more as the component (B1) and the content of the nonionic surfactant having an HLB of less than 11 as the component (B2), (B1)/(B2), is preferably from 0.1 to 25, more preferably from 0.6 to 20, further preferably from 0.8 to 16, further preferably from 1.5 to 14, further preferably from 2.5 to 12, further preferably from 5 to 12.

The content of the component (B) in the composition to be used is preferably 0.1 mass % or more, more preferably 0.4 mass % or more, further preferably 0.5 mass % or more; and preferably 30 mass % or less, more preferably 25 mass % or less, further preferably 20 mass % or less, further preferably 18 mass % or less, further preferably 15 mass % or less, further preferably 10 mass % or less from the viewpoint of exhibiting good sebum cleansing ability and makeup removability and further enhancing the keratotic plug-removing effect. The content of the component (B) in the composition to be used is preferably from 0.1 to 30 mass %, more preferably from 0.4 to 25 mass %, further preferably from 0.5 to 20 mass %, further preferably from 0.5 to 18 mass %, further preferably from 0.5 to 15 mass %, further preferably from 0.5 to 10 mass %.

In the composition of the present invention, the mass ratio of the content of the component (X) to the content of the component (B), (X)/(B), is preferably 0.01 or more, more preferably 0.02 or more, further preferably 0.03 or more, further preferably 0.1 or more, further preferably 0.3 or more, further preferably 0.5 or more from the viewpoint of exhibiting an excellent keratotic plug-removing effect and improving the sebum cleansing ability and the makeup removability. In the composition used in the present invention, the mass ratio of the content of the component (X) to the content of the component (B), (X)/(B), is preferably 50 or less, more preferably 30 or less, further preferably 25 or less, further preferably 20 or less, further preferably 15 or less from the viewpoint of exhibiting an excellent keratotic plug-removing effect. In the composition used in the present invention, the mass ratio of the content of the component (X) to the content of the component (B), (X)/(B), is preferably from 0.01 to 50, more preferably from 0.02 to 30, further preferably from 0.03 to 25, further preferably from 0.1 to 25, further preferably from 0.3 to 20, further preferably from 0.5 to 20, further preferably from 0.5 to 15.

The composition of the present invention can further contain (C) an ampholytic surfactant from the viewpoint of improving foaming property. Examples of the ampholytic surfactant include amide amino acid surfactants, carbobetaine surfactants, amidobetaine surfactants, amidosulfobetaine surfactants, and sulfobetaine surfactants.

Although the content of the ampholytic surfactant varies depending on the dosage form of the composition of the present invention, the content in the composition of the present invention is preferably 0.1 mass % or more, more preferably 0.5 mass % or more, further preferably 1 mass % or more and preferably 15 mass % or less, more preferably 10 mass % or less, and further preferably 5 mass % or less from the viewpoint of enhancing the keratotic plug-removing effect and imparting excellent foaming property. The content of the component (C) in the composition to be used is preferably from 0.1 to 15 mass %, more preferably from 0.5 to 10 mass %, further preferably from 1 to 5 mass %.

The composition of the present invention preferably further contains (D) a polyol from the viewpoint of imparting moist feeling to the skin while exhibiting an excellent keratotic plug-removing effect. Examples of the polyol as the component (D) include divalent alcohols such as ethylene glycol, diethylene glycol, polyethylene glycol, propylene glycol, dipropylene glycol, polypropylene glycol, isoprene glycol, hexylene glycol, and 1,3-butylene glycol; tri- or higher valent alcohols such as glycerol, diglycerol, triglycerol, tetraglycerol, hexaglycerol, decaglycerol, and trimethyl propanol; and sugars and sugar alcohols such as erythritol, pentaerythritol, dipentaerythritol, glucose, mannose, galactose, sucrose, fructose, maltose, trehalose, maltitol, xylitol, inositol, sorbitan, and sorbitol. In particular, from the viewpoint of imparting moist feeling to the skin and exhibiting an excellent keratotic plug-removing effect, component (D) includes preferably one or more selected from the group consisting of ethylene glycol, diethylene glycol, polyethylene glycol, propylene glycol, dipropylene glycol, polypropylene glycol, isoprene glycol, hexylene glycol, 1,3-butylene glycol, glycerol, diglycerol, triglycerol, tetraglycerol, hexaglycerol, decaglycerol, trimethyl propanol, erythritol, pentaerythritol, dipentaerythritol, glucose, mannose, galactose, sucrose, fructose, maltose, maltitol, xylitol, inositol, sorbitan, and sorbitol; preferably one or more selected from the group consisting of dipropylene glycol, 1,3-butylene glycol, glycerol, sorbitol, and mannitol.

The content of the component (D) in the composition to be used is preferably 0.5 mass % or more, more preferably 1.0 mass % or more, further preferably 3 mass % or more, further preferably 5 mass % or more, further preferably 8 mass % or more, further preferably 10 mass % or more; and preferably 40 mass % or less, more preferably 35 mass % or less, further preferably 30 mass % or less, further preferably 25 mass % or less, further preferably 20 mass % or less from the viewpoint of exhibiting an excellent keratotic plug-removing effect and imparting moist feeling to the skin. The content of the component (D) in the composition to be used is preferably from 0.5 to 40 mass %, more preferably from 1.0 to 35 mass %, further preferably from 3 to 30 mass %, further preferably from 5 to 25 mass %, further preferably from 8 to 20 mass %, further preferably from 10 to 20 mass %.

The composition of the present invention preferably further contains (E) a water-soluble polymer from the viewpoint of suppressing dropping during application and improving stability over time while exhibiting an excellent keratotic plug-removing effect. The water-soluble polymer as the component (E) may be any polymer that is generally used in known compositions.

Specifically, suitable examples of the water-soluble polymer include carboxyvinyl polymers, acrylic acid/alkyl (meth)acrylate copolymers, and cellulose to which a hydroxyethyl group or a hydroxypropyl group has been added, from the viewpoint of suppressing dropping during application and improving stability over time. The commercial products that can be used as the carboxyvinyl polymer are, for example, Carbopol 980 and Carbopol 981 (manufactured by Lubrizol Advanced Materials, Inc.). The commercial products that can be used as the acrylic acid/alkyl (meth)acrylate copolymer are, for example, Pemulen TR-1, Pemulen TR-2, Carbopol ETD2020, Carbopol 1382, Carbopol 1342, Carbopol Ultrez 10, Carbopol Ultrez 20, and Carbopol Ultrez 21 (manufactured by Lubrizol Advanced Materials, Inc.) and AQUPEC HV-501ER (manufactured by Sumitomo Seika Chemicals Co., Ltd.).

In the cellulose to which a hydroxyethyl group or a hydroxypropyl group has been added, hydrogen atoms in the hydroxyl groups of the cellulose are partially substituted with hydroxyethyl groups or hydroxypropyl groups, and the cellulose may have a substituent other than these substituents. Specifically, examples of such cellulose include hydroxyethyl cellulose, hydroxypropyl cellulose, hydroxyethyl methyl cellulose, and hydroxypropyl methyl cellulose. Such cellulose is prepared by reacting cellulose with sodium hydroxide to prepare alkali cellulose and subsequently applying, for example, methyl chloride, monochloroacetic acid, ethylene oxide, or propylene oxide to the alkali cellulose to substitute hydrogen atoms of the hydroxy groups in the cellulose with a hydroxyethyl group, hydroxypropyl group, methyl group, carboxymethyl group, etc.

The average degree of substitution of the cellulose is higher than 0, preferably 0.5 or more and preferably 3 or less, more preferably 2 or less from the viewpoint of suppressing dropping during application and improving stability over time. The weight average molecular weight is, from the same viewpoint as above, preferably 200,000 or more, more preferably 500,000 or more, more preferably 650,000 or more and preferably 3,000,000 or less, more preferably 2,000,000 or less, further preferably 1,600,000 or less. In the present invention, the average degree of substitution is determined by NMR, and the weight average molecular weight is measured with a gel permeation chromatography (GPC)-multiangle laser light scattering (MALLS) detection system using polyethylene oxide as a standard substance.

The cellulose to which a hydroxyethyl group or a hydroxypropyl group has been added is preferably hydroxyethyl cellulose or hydroxypropyl methyl cellulose having preferably an average degree of substitution of 0.5 to 2 and a weight average molecular weight of 650,000 to 1,600,000.

The cellulose to which a hydroxyethyl group or a hydroxypropyl group has been added can be a commercial product such as CELLOSIZE QP52000H (manufactured by The Dow Chemical Company) or HEC Daicel SE400, SE500, SE600, SE850, or SE900 (manufactured by Daicel FineChem Ltd.), as the hydroxyethyl cellulose; or METOLOSE 60SH or 65SH (manufactured by Shin-Etsu Chemical Co., Ltd.) or BENECEL E50, E4M, E10M, F4MC, K99C, K4M, K15M, K35M, K100M, or K200M (manufactured by ASHLAND Inc.) as the hydroxypropyl methyl cellulose.

The content of the component (E) in the composition to be used is preferably 0.01 mass % or more, more preferably 0.05 mass % or more, further preferably 0.10 mass % or more, further preferably 0.15 mass % or more and preferably 3 mass % or less, more preferably 2 mass % or less, further preferably 1.0 mass % or less, further preferably 0.8 mass % or less from the viewpoint of exhibiting an excellent keratotic plug-removing effect, suppressing dropping during application, and improving stability over time. The content of the component (E) in the composition to be used is preferably from 0.01 to 3 mass %, more preferably from 0.05 to 2 mass %, further preferably from 0.1 to 1.0 mass %, further preferably from 0.15 to 0.8 mass %.

The composition of the present invention preferably further contains (F) one or more selected from the group consisting of neutral amino acids, betaine compounds, and ethylenediamine tetraacetates from the viewpoint of imparting moist feeling to the skin while exhibiting an excellent keratotic plug-removing effect. Examples of the neutral amino acid as the component (F) include glycine, sarcosine, L-serine, β-alanine, and aminobutyric acid. Examples of the betaine compound other than the component (C) include trimethyl glycine, trimethyl serine, hydroxyethyl dimethyl glycine, and monoethanol-C5-carboxybetaine. In particular, from the viewpoint of exhibiting an excellent keratotic plug-removing effect, the component (F) includes preferably one or more selected from the group consisting of trimethyl glycine, trimethyl serine, hydroxyethyl dimethyl glycine, and monoethanol-C5-carboxybetaine; more preferably one or more selected from the group consisting of trimethyl glycine, trimethyl serine, and hydroxyethyl dimethyl glycine; further preferably trimethyl glycine.

The content of the component (F) in the composition to be used is preferably 0.1 mass % or more, more preferably 0.5 mass % or more, further preferably 1.0 mass % or more and preferably 20 mass % or less, more preferably 15 mass % or less, further preferably 10 mass % or less from the viewpoint of imparting moist feeling to the skin while exhibiting an excellent keratotic plug-removing effect. The content of the component (F) in the composition to be used is preferably from 0.1 to 20 mass %, more preferably from 0.5 to 15 mass %, further preferably from 1.0 to 10 mass %.

The composition of the present invention contains (G) water from the viewpoint of satisfactorily dissolving or dispersing the components mentioned above. The content of the water in the composition of the present invention is preferably 10 mass % or more, more preferably 20 mass % or more, further preferably 30 mass % or more and preferably 99.9 mass % or less, more preferably 99.5 mass % or less, further preferably 99 mass % or less.

The composition of the present invention can contain components that are generally used in known compositions, in addition to the above-described components, within a range not impairing the effects of the present invention. Examples of such components include oils such as hydrocarbon oils, ester oils, ether oils, and vegetable oils; moisturizing agents other than the components (D) and (E) such as sodium lactate, urea, and sodium pyrrolidone carboxylate; ultraviolet absorbers; antioxidants; disinfectants; extracts; perfumes; and dyes.

Each of these agents is not limited to its use as each agent and can be used as another application according to the purpose. For example, an antiperspirant is used as a perfume or can be used for more than one application, for example, an antiperspirant is used as an agent having effects as an antiperspirant and a perfume.

from the viewpoint of sufficiently exhibiting the keratotic plug-removing effect.

Furthermore, when the composition used in the present invention contains as the component (X), the pH of the composition at 25° C. is preferably, more preferably 8.8 or more, further preferably 9.0 or more, further preferably or more, further preferably, further preferably 9.8 or more, further preferably 10.0 or more from the viewpoint of sufficiently exhibiting the keratotic plug-removing effect of the component (X). The pH of the composition used in the present invention at 25° C. is preferably, more preferably 12.2 or less, further preferably 12.0 or less, further preferably 11.8 or less, further preferably 11.5 or less, further preferably 11.2 or less, further preferably 11 or less from the viewpoint of preventing an excessive burden on the skin. The pH of the composition used in the present invention at 25° C. is preferably from 8.6 to 12.5, more preferably from 8.8 to 12.2, further preferably from 9.0 to 12.0, further preferably from 9.2 to 11.8, further preferably from 9.3 to 11.8, further preferably from 9.5 to 11.5, further preferably from 9.8 to 11.2, further preferably from 10.0 to 11.0.

When the composition used in the present invention contains as the component (X), the pH of the composition at 25° C. is preferably, more preferably 9.2 or more, further preferably 9.3 or more, further preferably 9.5 or more, further preferably 9.8 or more, further preferably 10.0 or more, further preferably 10.2 or more, further preferably 10.5 or more from the viewpoint of sufficiently exhibiting the keratotic plug-removing effect of the component (X). The pH of the composition used in the present invention at 25° C. is preferably or less, more preferably 12.2 or less, further preferably 12.0 or less, further preferably 11.8 or less, further preferably 11.5 or less, further preferably 11.2 or less, further preferably 11.0 or less from the viewpoint of preventing an excessive burden on the skin. The pH of the composition used in the present invention at 25° C. is preferably from 9.0 to 12.5, more preferably from 9.2 to 12.2, further preferably from 9.3 to 12.2, further preferably from 9.5 to 12.0, further preferably from 9.8 to 11.8, further preferably from 10.0 to 11.5, further preferably from 10.2 to 11.5, further preferably from 10.2 to 11.2, further preferably from 10.5 to 11.2, further preferably from 10.5 to 11.0.

When the composition used in the present invention contains as the component (X), the pH of the composition at 25° C. is preferably, more preferably 8.8 or more, further preferably 9.0 or more, further preferably 9.2 or more, further preferably 9.3 or more, further preferably 9.5 or more, further preferably 9.8 or more, further preferably 10.0 or more, further preferably 10.2 or more, further preferably 10.5 or more from the viewpoint of sufficiently exhibiting the keratotic plug-removing effect of the component (X). The pH of the composition used in the present invention at 25° C. is preferably or less, more preferably 12.2 or less, further preferably 12.0 or less, further preferably 11.8 or less, further preferably 11.5 or less, further preferably 11.2 or less, further preferably 11.0 or less from the viewpoint of preventing an excessive burden on the skin. The pH of the composition used in the present invention at 25° C. is preferably from 8.5 to 12.5, more preferably from 8.8 to 12.2, further preferably from 9.0 to 12.0, further preferably from 9.2 to 11.8, further preferably from 9.3 to 11.8, further preferably from 9.5 to 11.5, further preferably from 9.8 to 11.5, further preferably from 10.0 to 11.5, further preferably from 10.2 to 11.2, further preferably from 10.5 to 11.2, further preferably from 10.5 to 11.0.

When the composition used in the present invention contains two or three selected from the group consisting of the components (X1) to (X3) as the component (X), the pH range showing an excellent keratotic plug-removing effect tends to be broadened, and the pH of the composition used in the present invention at 25° C. is preferably 8.3 or more, more preferably 8.5 or more, further preferably 8.8 or more, further preferably 9.0 or more, further preferably 9.2 or more, further preferably 9.3 or more, further preferably 9.5 or more, further preferably 9.8 or more, further preferably 10.0 or more from the viewpoint of sufficiently exhibiting the keratotic plug-removing effect of the component (X). The pH of the composition used in the present invention at 25° C. is preferably 12.5 or less, more preferably 12.2 or less, further preferably 12.0 or less, further preferably 11.8 or less, further preferably 11.5 or less, further preferably 11.2 or less, further preferably 11.0 or less from the viewpoint of preventing an excessive burden on the skin. The pH of the composition used in the present invention at 25° C. is preferably from 8.3 to 12.5, more preferably from 8.5 to 12.2, further preferably from 8.8 to 12.0, further preferably from 9.0 to 12.0, further preferably from 9.2 to 11.8, further preferably from 9.3 to 11.8, further preferably from 9.5 to 11.5, further preferably from 9.8 to 11.2, further preferably from 10.0 to 11.0.

The composition used in the present invention may appropriately contain a pH conditioner such as sodium hydroxide, sodium carbonate, sodium citrate, or hydrochloric acid.

The case of using a composition containing component (X) and component (Y) also tends to broaden the pH range showing an excellent keratotic plug-removing effect, and the pH of the composition used in the present invention at 25° C. is preferably 8.3 or more, more preferably 8.5 or more, further preferably 8.8 or more, further preferably 9.0 or more, further preferably 9.2 or more, further preferably 9.3 or more, further preferably 9.5 or more, further preferably 9.8 or more, further preferably 10.0 or more from the viewpoint of sufficiently exhibiting the keratotic plug-removing effect of the component (X). The pH of the composition used in the present invention at 25° C. is preferably 12.5 or less, more preferably 12.2 or less, further preferably 12.0 or less, further preferably 11.8 or less, further preferably 11.5 or less, further preferably 11.2 or less, further preferably 11.0 or less from the viewpoint of preventing an excessive burden on the skin. The pH of the composition used in the present invention at 25° C. is preferably from 8.3 to 12.5, more preferably from 8.5 to 12.2, further preferably from 8.8 to 12.0, further preferably from 9.0 to 12.0, further preferably from 9.2 to 11.8, further preferably from 9.3 to 11.8, further preferably from 9.5 to 11.5, further preferably from 9.8 to 11.2, further preferably from 10.0 to 11.0.

The composition used in the present invention may appropriately contain a pH conditioner, such as sodium hydroxide, sodium carbonate, sodium citrate, or hydrochloric acid.

The composition used in the present invention contains (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol as described above. The composition can be used as, for example, a cosmetic, a quasi-drug, or a medicine without any particular limitation. In particular, from the viewpoint of sufficiently benefiting from the excellent keratotic plug-removing effect, the composition can be used as a keratotic plug-removing composition or a keratotic plug-removing agent, can be suitably used as a pore-cleansing skin cosmetic for suppressing pore conspicuousness, and, in particular, can be suitably used as a keratotic plug-removing skin cosmetic for removing keratotic plugs.

The site to which the composition of the present invention is applied is preferably the skin of the body, more preferably the skin of, for example, face, neck, limbs, or torso, excluding the scalp, further preferably the pore sites on such skin, further preferably the pore sites on the skin from forehead to nose tip of the face. The composition can be used as follows: the composition is applied to such a desired site and, after a certain period of time, the composition remaining on the application site is washed away with water or is wiped away with a wiping material, such as tissue, nonwoven fabric, or woven fabric; preferably washed away with water.

Similarly, the composition can be suitably used as a skin cosmetic for improving skin brightness, in particular, as a skin cosmetic for improving skin dullness from the viewpoint of not only being capable of effectively removing keratotic plugs but also being capable of enhancing the brightness of the skin and reducing skin dullness. That is, application of such a cosmetic material to the skin can enhance the utility of the composition as a method for improving skin brightness or a method for improving skin dullness.

The composition can further be suitably used as an external preparation for suppressing acne from the viewpoint of effectively removing keratotic plugs and eliminating the cause of acne. That is, application of such an external preparation to the skin can enhance the utility of the composition as a method for suppressing acne.

The composition can further be suitably used as a composition for promoting skin penetration from the viewpoint of promoting penetration of an agent from pores by effectively removing keratotic plugs for exhibiting the effect of enhancing the action of the agent. That is, application of such a composition to the skin can enhance the utility of the composition as a method for promoting skin penetration.

The composition can also suppress protein aggregation and therefore can be suitably used as a protein aggregation suppresser. Application of such a composition to the skin can enhance the utility of the composition as a method for suppressing protein aggregation.

The dosage form of the composition used in the present invention is not particularly limited and is preferably a foam, liquid, paste, cream, or some other dosage form, more preferably a foam or liquid dosage form from the viewpoint of improving the penetration into keratotic plugs. The composition used in the present invention can be suitably applied as a hair cosmetic such as shampoo, rinse, or conditioner; and a skin cosmetic such as facial cleanser, makeup cleansing cosmetic, body cleanser, scalp cleanser, lotion, milky lotion, cream, essence, sunscreen cosmetic, pack, or massage cosmetic. Among these cosmetics, the composition is preferably applied as a skin cleanser such as facial cleanser, makeup cleansing cosmetic, body cleanser, and scalp cleanser.

The use form of the composition used in the present invention can be appropriately selected depending on, for example, the application site. For example, when the dosage form of the composition of the present invention is a liquid, paste, cream, or some other dosage form, the composition may be directly applied to the application site. Specifically, the composition is applied to an application site in an amount of preferably from 0.05 to 2 mL/cm$^2$, more preferably from 0.1 to 1 mL/cm$^2$; the application site is then massaged for usually from 10 seconds to 10 minutes, preferably from 15 seconds to 5 minutes, more preferably from 30 seconds to 4 minutes, further preferably from 1 to 3 minutes; and the composition remaining on the application site is subsequently washed away with water or wiped away with a wiping material such as tissue, nonwoven fabric, or woven fabric; desirably washed away with water.

For example, when the dosage form of the composition used in the present invention is a liquid dosage form, the composition can also be used as a sheet-form cleansing agent by impregnating a sheet material such as nonwoven fabric or woven fabric, with the composition. Specifically, a sheet-form cleansing agent impregnated with the composition is attached onto an application site and is left to stand for usually from 1 to 30 minutes, preferably from 5 to 20 minutes, further preferably from 10 to 15 minutes, and the sheet-from cleansing agent is then peeled off. The composition remaining on the application site is then washed away with water or wiped away with a wiping material such as tissue, nonwoven fabric, or woven fabric, desirably washed away with water.

Furthermore, when the composition used in the present invention is in a foam dosage form, for example, a foam discharge container is filled with the composition in the liquid form, and the composition may be discharged from the container onto the application site in use. After the discharging, the same procedure as that in the use form of the application may be carried out. Such a foam dosage form is suitable for massaging the application site.

A spray container or high-pressure washer is filled with the composition used in the present invention, and the composition may be sprayed from the nozzle in use. In such a case, the composition is sprayed onto the application site for usually from 10 seconds to 5 minutes, preferably from 15 seconds to 3 minutes, further preferably from 30 seconds to 2 minutes to wash the application site. Subsequently, the composition remaining on the application site is then washed away with water or wiped away with a wiping material such as tissue, nonwoven fabric, or woven fabric, desirably washed away with water.

The composition used in the present invention can be prepared by, for example, a production process including step (I) of heating water to 60° C. to 80° C. in advance, step (II) of sequentially adding the component (X) and other components as needed to the water obtained in step (I) and mixing and stirring, and step (III) of cooling the mixture obtained in step (II) to 20° C. to 35° C.

When an acidic component such as an unneutralized fatty acid is present as the other components to be used, the component (X) is consumed for neutralizing the negative charge, resulting in a risk of decreasing the content of the component (X) in a free-form in the resulting composition to a level lower than a predetermined amount. Accordingly, the step (II) is desirably a step for which the decrease is added. That is, the step (II) is preferably performed as step (II)' of sequentially mixing the components other than the component (X) and mixing and stirring for dissolving each component before addition of the component (X), subsequently adding a neutralizer to the mixture for neutralizing the acidic component, and then adding the component (X) and mixing and stirring for dissolution, followed by step (III).

Alternatively, the acidic component may be directly neutralized with the component (X) without using any neutralizer, unlike step (II)'. That is, the step (II) may be performed as step (II)" of sequentially mixing the components other than the component (X) and mixing and stirring for dissolving each component before addition of the component (X), adding the component (X) for neutralizing the acidic component, and then mixing and stirring for dissolution, followed by step (III). In this case, the amount of the component (X) added in step (II)" may be the sum of the content of the component (X) in free-form in the resulting composition and the amount of the component (X) necessary for neutralizing the acidic component.

Even in the case of preparing a composition containing both of the component (X) and the component (Y), the component (Y) is desirably treated as in the component (X).

Regarding the above-described embodiments, the present invention further discloses methods for removing keratotic plugs using the following compositions and compositions for removing keratotic plugs.

[1] A method for removing keratotic plugs using a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[2] The method for removing keratotic plugs according to above [1], wherein when one component is used as the component (X), the composition comprises preferably (X3) 2-amino-2-hydroxymethyl-1,3-propanediol; and when two components are used as the component (X), the composition comprises one selected from the group consisting of (X1) 2-amino-2-hydroxymethyl-1,3-propanediol and (X2) 2-amino-2-methyl-1-propanol, and (X3) 2-amino-2-methyl-1,3-propanediol.

[3] The method for removing keratotic plugs according to above [1] or [2], wherein the total content of component (X) in the composition is preferably 0.08 mass % or more, more preferably 0.10 mass % or more, further preferably 0.5 mass % or more, further preferably 0.8 mass % or more, further preferably 1.0 mass % or more, further preferably 2 mass % or more, further preferably 3 mass % or more, further preferably 4 mass % or more, further preferably 5 mass % or more; and preferably 35 mass % or less, more preferably 30 mass % or less, further preferably 25 mass % or less, further preferably 20 mass % or less, further preferably 15 mass % or less, further preferably 12 mass % or less, further preferably 11 mass % or less, further preferably 10 mass % or less.

[4] The method for removing keratotic plugs according to any one of above [1] to [3], wherein the mass ratio of the content of the component (X) present in a free form to the content of the component (X), (content of free-form component (X))/(content of component (X)), is preferably 0.6 or more, more preferably 0.8 or more, further preferably 0.9 or more.

[5] The method for removing keratotic plugs according to any one of above [1] to [4], wherein the composition further comprises (Y) a basic substance other than the component (X), and the total content of component (Y) in the composition is preferably 0.01 mass % or more, more preferably 0.05 mass % or more, further preferably 0.10 mass % or more and preferably 15 mass % or less, more preferably 12 mass % or less, further preferably 10 mass % or less.

[6] The method for removing keratotic plugs according to above [5], wherein the component (Y) comprises one or more selected from the group consisting of linear or cyclic aliphatic amines, basic amino acids, inorganic salts each composed of a strong base and a weak acid, and aromatic amines; preferably one or more selected from the group consisting of aliphatic amines and basic amino acids; more preferably one or more selected from the group consisting of arginine, monoethanolamine, triethanolamine, and morpholine; further preferably one or two selected from the group consisting of arginine and triethanolamine; further preferably arginine.

[7] The method for removing keratotic plugs according to above [5] or [6], wherein the total content of the component (X) and the component (Y) in the composition is preferably 50 mass % or less, more preferably 32 mass % or less, more preferably 25 mass % or less, further preferably 20 mass % or less, further preferably 15 mass % or less, further preferably 12 mass % or less; and preferably 0.09 mass % or more, more preferably 0.15 or more, further preferably 0.50 mass % or more, further preferably 1.0 mass % or more, more preferably 2 mass % or more, further preferably 3 mass % or more, further preferably 5 mass; or more, further preferably higher than 5 mass %.

[8] The method for removing keratotic plugs according to any one of above [5] to [7], wherein the mass ratio of the content of the component (X) to the content of the component (Y), (X)/(Y), is preferably 0.001 or more, more preferably 0.005 or more, further preferably 0.008 or more, further preferably 0.01 or more; and preferably 200 or less, more preferably 150 or less, further preferably 120 or less, further preferably 100 or less.

[9] The method for removing keratotic plugs according to any one of above [5] to [8], wherein the mass ratio of the content of the component (Y) present in a free form to the content of the component (Y), (content of free-form component (Y)/content of component (Y)), is preferably 0.6 or more, more preferably 0.8 or more, further preferably 0.9 or more, further preferably 1.0.

[10] The method for removing keratotic plugs according to any one of above [1] to [9], wherein the composition further comprises (A) an anionic surfactant, and the component (A) preferably comprises (A1) an anionic surfactant having a carboxylic acid group and/or (A2) an anionic surfactant having a sulfonic acid group or a sulfate group.

[11] The method for removing keratotic plugs according to above [10], wherein preferably comprises one or more selected from the group consisting of fatty acids or salts thereof, ether carboxylic acids or salts thereof, and N-acylamino acid salts; and the component (A2) preferably comprises one or more selected from the group consisting of alkylbenzene sulfonic acids or salts thereof, alkanesulfonic acids or salts thereof, alkenylsulfonic acids or salts thereof, alkylsulfonic acids or salts thereof, acylisethionic acids or salts thereof, alkyl sulfate or salts thereof, alkyl ether sulfates or salts thereof, alkyl sulfosuccinic acids or salts thereof, sulfofatty acid methyl esters or salts thereof, fatty acid alkanolamide sulfates or salts thereof, and monoacylglycerol sulfates or salts thereof.

[12] The method for removing keratotic plugs according to above [10] or [11], wherein the mass ratio of the content of the component (X) to the content of the component (A1), (X)/(A1), is preferably 0.1 or more, more preferably 0.5 or more, further preferably 1.0 or more; and preferably 100 or less, more preferably 80 or less, and further preferably 70 or less; in particular, when the component (X) is either of the component (X1) or (X2), the mass ratio is further preferably 2 or more, further preferably 5 or more, further preferably 8 or more; and further preferably 60 or less, further preferably 50 or less, further preferably 40 or less, further preferably 30 or less, further preferably 20 or less; when the component (X) is the component (X3) only, the mass ratio is further preferably 2 or more, further preferably 5 or more, further preferably 8 or more, further preferably 15 or more, further preferably 30 or more, further preferably 40 or more; and further preferably 68 or less, further preferably 65 or less, further preferably 62 or less, further preferably 60 or less; or the mass ratio of the content of the component (X) to the content of the component (A2), (X)/(A2), is preferably from 0.005 to 100, more preferably from 0.01 to 60, further preferably from 0.10 to 50, further preferably from 0.20 to 40, further preferably from 0.20 to 30, further preferably from 0.20 to 20, further preferably from 0.25 to 15, further preferably from 0.3 to 14, further preferably from 0.50 to 12.5.

[13] The method for removing keratotic plugs according to any one of above [10] to [12], wherein the content of the component (A1) in the composition is preferably 0.01 mass % or more, more preferably 0.05 mass % or more, further preferably 0.10 mass % or more, further preferably 0.3 mass % or more; and preferably 5 mass % or less, more preferably 3 mass; or less, further preferably 2.0 mass' or less, further preferably 1.5 mass % or less, further preferably 1.0 mass % or less; or the content of the component (A2) is preferably 0.01 mass % or more, more preferably 0.03 mass % or more, further preferably 0.05 mass % or more, further preferably 0.10 mass % or more; and preferably 20 mass % or less, more preferably 18 mass % or less, further preferably 15 mass % or less; in particular, when the component (X) is either of the component (X1) or the component (X2), the content is further preferably 0.2 mass % or more, further preferably 0.3 mass % or more, further preferably 0.5 mass % or more; and further preferably 12 mass % or less, further preferably 10 mass'S or less, further preferably 8 mass % or less, further preferably 5 mass % or less, further preferably 4 mass % or less, further preferably 3 mass % or less; when the component (X) is the component (X3) only, the content is preferably 0.2 mass % or more, further preferably 0.3 mass % or more, further preferably 0.5 mass % or more, further preferably 1.0 mass % or more, further preferably 1.5 mass % or more, further preferably 2.0 mass % or more; and preferably 14 mass % or less, more preferably 13 mass % or less, further preferably 12 mass % or less, further preferably 11 mass % or less, further preferably 10 mass % or less.

[14] The method for removing keratotic plugs according to any one of above [10] to [13], wherein the total content of the component (A) in the composition is preferably 0.01 mass % or more, more preferably 0.02 mass % or more, further preferably 0.05 mass % or more, further preferably 0.1 mass % or more, further preferably 0.3 mass % or more, further preferably 0.5 mass % or more; and preferably 30 mass % or less, more preferably 20 mass % or less, further preferably 15 mass %, further preferably 12 mass % or less, further preferably 8 mass % or less, further preferably 4 mass % or less.

[15] The method for removing keratotic plugs according to any one of above [1] to [14], wherein the content of the anionic surfactant other than the components (A1) and (A2) in the composition is preferably 0.01 mass % or more, more preferably 0.05 mass % or more, further preferably 0.1 mass % or more; and preferably 10 mass % or less, more preferably 5 mass % or less, further preferably 1.0 mass % or less, further preferably 0.5 mass % or less.

[16] The method for removing keratotic plugs according to any one of above [1] to [15], wherein the composition further comprises (B) a nonionic surfactant, preferably (B1) a nonionic surfactant having an HLB of 11 or more and/or (B2) a nonionic surfactant having an HLB of less than 11 as the component (B).

[17] The method for removing keratotic plugs according to above [16], wherein the component (B1) comprises preferably one or more selected from the group consisting of polyglycerol fatty acid esters, polyethylene glycol fatty acid esters, polyoxyethylene alkyl ethers, polyoxyethylene glycerol fatty acid esters, polyoxyethylene sorbitan fatty acid esters, polyoxyethylene hydrogenated castor oil fatty acid esters, and alkyl polyglucosides, more preferably one or more selected from the group consisting of polyethylene glycol fatty acid esters, polyoxyethylene alkyl ethers, polyoxyethylene sorbitan fatty acid esters, and alkyl polyglucosides.

[18] The method for removing keratotic plugs according to above [16] or [17], wherein the component (B2) preferably comprises one or more selected from the group consisting of polyoxyethylene alkyl ethers and polyglycerol fatty acid esters.

[19] The method for removing keratotic plugs according to any one of above [16] to [18], wherein the content of the component (B) in the composition is preferably 0.1 mass % or more, more preferably 0.4 mass % or more, further preferably 0.5 mass % or more; and preferably 30 mass % or less, more preferably 25 mass % or less, further preferably 20 mass % or less, further preferably 15 mass % or less, further preferably 10 mass % or less.

[20] The method for removing keratotic plugs according to any one of above [16] to [19], wherein the mass ratio of the content of the component (B1) to the content of the component (B2), (B1)/(B2), is preferably 0.1 or more, more preferably 0.6 or more, further preferably 0.8 or more, further preferably 1.5 or more, further preferably 2.5 or more, further preferably 5 or more; and preferably 25 or less, more preferably 20 or less, further preferably 16 or less, further preferably 14 or less, further preferably 12 or less.

[21] The method for removing keratotic plugs according to any one of above [16] to [20], wherein the mass ratio of the content of the component (X) to the content of the component (B), (X)/(B), is preferably 0.01 or more, more preferably 0.1 or more, further preferably 0.3 or more, further preferably 0.5 or more; and preferably 50 or less, more preferably 30 or less, further preferably 25 or less, further preferably 20 or less, further preferably 15 or less.

[22] The method for removing keratotic plugs according to any one of above [1] to [21], wherein the composition further comprises (C) an ampholytic surfactant, and the content of the component (C) in the composition is preferably 0.1 mass % or more, more preferably 0.5 mass % or more, further preferably 1 mass % or more; and preferably 15 mass % or less, more preferably 10 mass % or less, further preferably 5 mass % or less.

[23] The method for removing keratotic plugs according to any one of above [1] to [22], wherein the composition further comprises (D) a polyol, and the content of the component (D) in the composition is preferably 0.5 mass % or more, more preferably 1 mass % or more, further preferably 3 mass % or more, further preferably 5 mass % or more, further preferably 8 mass % or more, further preferably 10 mass % or more; and preferably 40 mass % or less, more preferably 35 mass % or less, further preferably 30 mass % or less, further preferably 25 mass % or less, further preferably 20 mass % or less.

[24] The method for removing keratotic plugs according to above [23], wherein the component (D) comprises preferably one or more selected from the group consisting of ethylene glycol, diethylene glycol, polyethylene glycol, propylene glycol, dipropylene glycol, polypropylene glycol, isoprene glycol, hexylene glycol, 1,3-butylene glycol, glycerol, diglycerol, triglycerol, tetraglycerol, hexaglycerol, decaglycerol, trimethyl propanol, erythritol, pentaerythritol, dipentaerythritol, glucose, mannose, galactose, sucrose, fructose, maltose, maltitol, xylitol, inositol, sorbitan, and sorbitol; more preferably one or more selected from the group consisting of dipropylene glycol, 1,3-butylene glycol, glycerol, sorbitol, and mannitol.

[25] The method for removing keratotic plugs according to any one of above [1] to [24], wherein the composition further comprises (E) a water-soluble polymer, and the content of the component (E) in the composition is preferably 0.01 mass % or more, more preferably 0.05 mass'S or more, further preferably 0.10 mass % or more, further preferably 0.15 mass % or more; and preferably 3 mass % or less, more preferably 2 mass % or less, further preferably 1.0 mass % or less, further preferably 0.8 mass % or less.

[26] The method for removing keratotic plugs according to above [25], wherein the component (E) comprises one or more selected from the group consisting of carboxyvinyl polymers, acrylic acid/alkyl (meth)acrylate copolymers, and cellulose to which a hydroxyethyl group or a hydroxypropyl group has been added.

[27] The method for removing keratotic plugs according to any one of above [1] to [26], wherein the composition further contains component (F) one or more selected from the group consisting of neutral amino acids, betaine compounds, and ethylenediamine tetraacetate, and the content of the component (F) in the composition is preferably 0.1 mass % or more, more preferably 0.5 mass % or more, further preferably 1.0 mass % or more; and preferably 20 mass % or less, more preferably 15 mass % or less, further preferably 10 mass % or less.

[28] The method for removing keratotic plugs according to above [27], wherein the component (F) comprises preferably one or more selected from the group consisting of trimethyl glycine, trimethyl serine, hydroxyethyl dimethyl glycine, and monoethanol-C5-carboxybetaine; more preferably one or more selected from the group consisting of trimethyl glycine, trimethyl serine, and hydroxyethyl dimethyl glycine, further preferably trimethyl glycine.

[29] The method for removing keratotic plugs according to any one of above [1] to [28], wherein the composition comprises (G) water, and the content of the component (G) is preferably 10 mass % or more, more preferably 20 mass % or more, further preferably 30 mass % or more; and preferably 99.9 mass % or less, more preferably 99.5 mass % or less, further preferably 99 mass % or less.

[30] The method for removing keratotic plugs according to any one of above [1] to [29], wherein when the composition comprises any one of the component (X) alone, the pH of the composition at 25° C. is preferably 8.5 or more and preferably 12.5 or less.

[31] The method for removing keratotic plugs according to any one of above [1] to [30], wherein when the composition comprises (X1) 2-amino-2-hydroxymethyl-1,3-propanediol alone as the component (X), the pH of the composition at 25° C. is preferably 8.6 or more, more preferably 8.8 or more, further preferably 9.0 or more, further preferably 9.2 or more, further preferably 9.3 or more, further preferably 9.5 or more, further preferably 9.8 or more, further preferably 10.0 or more; and preferably 12.5 or less, more preferably 12.2 or less, further preferably 12.0 or less, further preferably 11.8 or less, further preferably 11.5 or less, further preferably 11.2 or less, further preferably 11 or less.

[32] The method for removing keratotic plugs according to any one of above [1] to [30], wherein when the composition comprises (X2) 2-amino-2-methyl-1-propanol alone as the component (X), the pH of the composition at 25° C. is preferably 9.0 or more, more preferably 9.2 or more, further preferably 9.3 or more, further preferably 9.5 or more, further preferably 9.8 or more, further preferably 10.0 or more, further preferably 10.2 or more, further preferably 10.5 or more; and preferably 12.5 or less, more preferably 12.2 or less, further preferably 12.0 or less, further preferably 11.8 or less, further preferably 11.5 or less, further preferably 11.2 or less, further preferably 11.0 or less.

[33] The method for removing keratotic plugs according to any one of above [1] to [30], wherein when the composition comprises (X3) 2-amino-2-methyl-1,3-propanediol alone as the component (X), the pH of the composition at 25° C. is preferably 8.5 or more, more preferably 8.8 or more, further preferably 9.0 or more, further preferably 9.2 or more, further preferably 9.3 or more, further preferably 9.5 or more, further preferably 9.8 or more, further preferably 10.0 or more; and preferably 12.5 or less, more preferably 12.2 or less, further preferably 12.0 or less, further preferably 11.8 or less, further preferably 11.5 or less, further preferably 11.2 or less, further preferably 11 or less.

[34] The method for removing keratotic plugs according to any one of above [1] to [29], wherein when the composition comprises two or more selected from the group consisting of the components (X1) to (X3) as the component (X), the pH of the composition at 25° C. is preferably 8.3 or more, more preferably 8.5 or more, further preferably 8.8 or more, further preferably 9.0 or more, further preferably 9.2 or more, further preferably 9.3 or more, further preferably 9.5 or more, further preferably 9.8 or more, further preferably 10.0 or more.

[35] The method for removing keratotic plugs according to any one of above [5] to [8], wherein when the composition comprises the component (X) and the component (Y), the pH of the composition at 25° C. is preferably 8.3 or more, more preferably 8.5 or more, further preferably 8.8 or more, further preferably 9.0 or more, further preferably 9.2 or more, further preferably 9.3 or more, further preferably 9.5 or more, further preferably 9.8 or more, further preferably 10.0 or more; and preferably 12.5 or less, more preferably 12.2 or less, further preferably 12.0 or less, further preferably 11.8 or less, further preferably 11.5 or less, further preferably 11.2 or less, further preferably 10.0 or less.

[36] The method for removing keratotic plugs according to any one of above [1] to [35], wherein the composition is preferably in a foam, liquid, paste, or cream dosage form, more preferably in a foam or liquid dosage form.

[37] A method for cleansing skin, comprising applying a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol to the skin, and after a certain period of time, washing away the composition with water or wiping away the composition with a wiping material.

[38] A method for cleansing pores, comprising applying a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol to the skin, and after a certain period of time, washing away the composition with water or wiping away the composition with a wiping material.

[39] A method for removing keratotic plugs, comprising applying a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol to the skin, and after a certain period of time, washing away the composition with water or wiping away the composition with a wiping material.

[40] A method for suppressing protein aggregation, comprising applying a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol to the skin.

[41] A method for improving skin brightness or a method for improving skin dullness, comprising applying a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol to the skin.

[42] A method for suppressing acne, comprising applying a composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol to the skin.

[43] A composition for removing keratotic plugs, comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[44] A protein aggregation suppresser comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[45] A skin cosmetic for cleansing pores, comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[46] A skin external preparation for suppressing acne, comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[47] A composition for promoting skin penetration, comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[48] Use of a composition for removing keratotic plugs, the composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[49] Use of a composition for suppressing protein aggregation, the composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[50] Use of a composition for cleansing pores, the composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[51] Use of a composition for suppressing acne, the composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[52] Use of a composition for promoting skin penetration, the composition comprising (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol.

[53] A method for producing the composition according to any one of above [1] to [52], the method comprising step (I) of heating water to 60° C. to 80° C. in advance, step (II) of sequentially adding the component (X) and other components as needed to the water obtained in step (I) followed by mixing and stirring, and step (III) of cooling the mixture obtained in step (II) to 20° C. to 35° C.

[54] The method for producing a composition according to above [53], wherein the composition comprises an acidic component, and step (II) comprises step (II1') of sequentially mixing components comprising the acidic component other than the component (X) followed by mixing and stirring for dissolving each component, step (II2') of subsequently adding a neutralizer thereto for neutralizing the acidic component, and step (II3') of subsequently adding the component (X) and the component (Y) as needed followed by mixing and stirring for dissolution.

[55] The method for producing the composition according to above [54], wherein the neutralizer is one or two selected from the group consisting of sodium hydroxide and potassium hydroxide.

[56] The method for producing the composition according to above [53], wherein the composition comprises an acidic component, and step (II) comprises step (II1') of sequentially mixing components comprising the acidic component other than the component (X), followed by mixing and stirring for dissolving each component and step (II2') of subsequently adding the component (X) in an amount equal to or higher than that necessary for neutralizing the acidic component and the component (Y) as needed followed by mixing and stirring for dissolution.

[57] A method for using a composition, comprising applying the composition according to any one of above [43] to [47] to preferably the skin of the body, more preferably the skin of the face, neck, limbs, or torso, excluding the scalp, further preferably the pore sites on the skin, further preferably the pore sites on the skin from the forehead to the nose tip of the face; and, after a certain period of time, washing away the composition with water or wiping away the composition with a wiping material.

[58] The method for using a composition according to above [57], wherein the application site is massaged for from 10 seconds to 10 minutes, preferably from 15 seconds to 5 minutes, more preferably from 30 seconds to 4 minutes, further preferably 1 to 3 minutes; and subsequently washing away the composition remaining on the application site with water or wiping away the composition remaining on the application site with a wiping material.

[59] The method for removing keratotic plugs or the use of a composition for removing keratotic plugs according to any one of above [1] to [36] and [48], wherein the composition comprises any one of the component (X); the pH of the composition at 25° C. is 8.5 or more and 12.5 or less; and the content of the component (X) in the composition is 0.08 mass % or more and 35 mass % or less.

[60] The method for removing keratotic plugs or the use of a composition for removing keratotic plugs according to any one of above [1] to [36], [48], and [59], wherein the composition comprises any one of the component (X); the pH of the composition at 25° C. is 8.5 or more and 12.5 or less; and the content of the component (X) in the composition is 1.0 mass % or more and 20 mass % or less.

[61] The method for removing keratotic plugs or the use of a composition for removing keratotic plugs according to any one of above [1] to [36], [48], [59], and [60], wherein the composition comprises any one of the component (X); the pH of the composition at 25° C. is 8.5 or more and 12.5 or less; and the content of the component (X) in the composition is 3 mass % or more and 12 mass % or less.

[62] The method for removing keratotic plugs or the use of a composition for removing keratotic plugs according to any one of above [1] to [36], [48], and [59] to [61], wherein the composition comprises any one of the component (X); the pH of the composition at 25° C. is 8.5 or more and 12.5 or less; and the content of the component (X) in the composition is 5 mass' or more and 10 mass % or less.

[63] The method for removing keratotic plugs or the use of a composition for removing keratotic plugs according to any one of above [1] to [36], [48], and [59] to [62], wherein the composition comprises any two or more of the component (X); the pH of the composition at 25° C. is 8.3 or more

[64] The method for removing keratotic plugs or the use of a composition for removing keratotic plugs according to any one of above [1] to [36], [48], and [59] to [63], wherein the composition comprises any two or more of the component (X); the pH of the composition at 25° C. is 8.3 or more and 12.5 or less; and the total content of the component (X) in the composition is 1.0 mass % or more and 20 mass % or less.

[65] The method for removing keratotic plugs or the use of a composition for removing keratotic plugs according to any one of above [1] to [36], [48], and [59] to [64], wherein the composition comprises any two or more of the component (X); the pH of the composition at 25° C. is 8.3 or more and 12.5 or less; and the total content of the component (X) in the composition is 3 mass % or more and 12 mass % or less.

[66] The method for removing keratotic plugs or the use of a composition for removing keratotic plugs according to any one of above [1] to [36], [48], and [59] to [65], wherein the composition comprises any two or more of the component (X); the pH of the composition at 25° C. is 8.3 or more and 12.5 or less; and the total content of the component (X) in the composition is 5 mass % or more and 10 mass % or less.

[67] The method for removing keratotic plugs or the use of a composition for removing keratotic plugs according to any one of above [1] to [36], [48], and [59] to [66], wherein the composition comprises the component (X1); the pH of the composition at 25° C. is 8.5 or more and 12.5 or less; and the content of the component (X) in the composition is 0.08 mass % or more and 35 mass % or less.

[68] The method for removing keratotic plugs or the use of a composition for removing keratotic plugs according to any one of above [1] to [36], [48], and [59] to [67], wherein the composition comprises the component (X1); the pH of the composition at 25° C. is 8.5 or more and 12.5 or less; and the content of the component (X) in the composition is 1.0 mass % or more and 20 mass % or less.

[69] The method for removing keratotic plugs or the use of a composition for removing keratotic plugs according to any one of above [1] to [36], [48], and [59] to [68], wherein the composition comprises the component (X1); the pH of the composition at 25° C. is 8.5 or more and 12.5 or less; and the content of the component (X) in the composition is 3 mass % or more and 12 mass % or less.

[70] The method for removing keratotic plugs or the use of a composition for removing keratotic plugs according to any one of above [1] to [36], [48], and [59] to [69], wherein the composition comprises the component (X1); the pH of the composition at 25° C. is 8.5 or more and 12.5 or less; and the content of the component (X) in the composition is 5 mass % or more and 10 mass % or less.

[71] The method for removing keratotic plugs or the use of a composition for removing keratotic plugs according to any one of above [1] to [36], [48], and [59] to [70], wherein the composition comprises the component (X2); the pH of the composition at 25° C. is 9.0 or more and 12.5 or less; and the content of the component (X) in the composition is 0.08 mass % or more and 35 mass % or less.

[72] The method for removing keratotic plugs or the use of a composition for removing keratotic plugs according to any one of above [1] to [36], [48], and [59] to [71], wherein the composition comprises the component (X2); the pH of the composition at 25° C. is 9.0 or more and 12.5 or less; and the content of the component (X) in the composition is 1.0 mass % or more and 20 mass % or less.

[73] The method for removing keratotic plugs or the use of a composition for removing keratotic plugs according to any one of above [1] to [36], [48], and [59] to [72], wherein the composition comprises the component (X2); the pH of the composition at 25° C. is 9.0 or more and 12.5 or less; and the content of the component (X) in the composition is 3 mass % or more and 12 mass % or less.

[74] The method for removing keratotic plugs or the use of a composition for removing keratotic plugs according to any one of above [1] to [36], [48], and [59] to [73], wherein the composition comprises the component (X2); the pH of the composition at 25° C. is 9.0 or more and 12.5 or less; and the content of the component (X) in the composition is 5 mass % or more and 10 mass % or less.

[75] The method for removing keratotic plugs or the use of a composition for removing keratotic plugs according to any one of above [1] to [36], [48], and [59] to [74], wherein the composition comprises the component (X3); the pH of the composition at 25° C. is 8.5 or more and 12.5 or less; and the content of the component (X) in the composition is 0.08 mass % or more and 35 mass % or less.

[76] The method for removing keratotic plugs or the use of a composition for removing keratotic plugs according to any one of above [1] to [36], [48], and [59] to [75], wherein the composition comprises the component (X3); the pH of the composition at 25° C. is 8.5 or more and 12.5 or less; and the content of the component (X) in the composition is 1.0 mass % or more and 20 mass % or less.

[77] The method for removing keratotic plugs or the use of a composition for removing keratotic plugs according to any one of above [1] to [36], [48], and [59] to [76], wherein the composition comprises the component (X3); the pH of the composition at 25° C. is 8.5 or more and 12.5 or less; and the content of the component (X) in the composition is 3 mass % or more and 12 mass % or less.

[78] The method for removing keratotic plugs or the use of a composition for removing keratotic plugs according to any one of above [1] to [36], [48], and [59] to [77], wherein the composition comprises the component (X3); the pH of the composition at 25° C. is 8.5 or more and 12.5 or less; and the content of the component (X) in the composition is 5 mass % or more and 10 mass % or less.

[79] The method for removing keratotic plugs or the use of a composition for removing keratotic plugs according to any one of above [1] to [36], [48], and [59] to [78], wherein the composition comprises one selected from the group consisting of the component (X1) and the component (X2), and the component (X3); the mass ratio of the content of the component (X3) to the total content of the component (X1) and the component (X2), (X3)/((X1)+(X2)), is 0.001 or more and 100 or less; the pH of the composition at 25° C. is 8.5 or more and 12.5 or less; and the content of the component (X) in the composition is 0.08 mass % or more and 35 mass; or less.

[80] The method for removing keratotic plugs or the use of a composition for removing keratotic plugs according to any one of above [1] to [36], [48], and [59] to [79], wherein the composition comprises one selected from the group consisting of the component (X1) and the component (X2), and the component (X3); the mass ratio of the content of the component (X3) to the total content of the component (X1) and the component (X2), (X3)/((X1)+(X2)), is 0.05 or more and 50 or less; the pH of the composition at 25° C. is 8.5 or more and 12.5 or less; and the content of the component (X) in the composition is 1.0 mass' or more and 20 mass' or less.

[81] The method for removing keratotic plugs or the use of a composition for removing keratotic plugs according to any one of above [1] to [36], [48], and [59] to [80], wherein the component (X) comprises one selected from the group consisting of the component (X1) and the component (X2), and the component (X3); the mass ratio of the content of the component (X3) to the total content of the component (X1) and the component (X2), (X3)/((X1)+(X2)), is 0.08 or more and 20 or less; the pH of the composition at 25° C. is 8.5 or more and 12.5 or less; and the content of the component (X) in the composition is 3 mass % or more and 12 mass % or less.

[82] The method for removing keratotic plugs or the use of a composition for removing keratotic plugs according to any one of above [1] to [36], [48], and [59] to [81], wherein the composition comprises one selected from the group consisting of the component (X1) and the component (X2), and the component (X3); the mass ratio of the content of the component (X3) to the total content of the component (X1) and the component (X2), (X3)/((X1)+(X2)), is 0.10 or more and 10 or less; the pH of the composition at 25° C. is 8.5 or more and 12.5 or less; and the content of the component (X) in the composition is 5 mass % or more and 10 mass' or less.

[83] The method for removing keratotic plugs or the use of a composition for removing keratotic plugs according to any one of above [1] to [36], [48], and [59] to [82], wherein the composition comprises the component (X) and the component (Y); the mass ratio of the content of the component (X) to the content of the component (Y), (X)/(Y), is 0.001 or more and 200 or less; the pH of the composition at 25° C. is 8.3 or more and 12.5 or less; and the total content of the component (X) and the component (Y) in the composition is 0.09 mass % or more and 50 mass % or less.

[84] The method for removing keratotic plugs or the use of a composition for removing keratotic plugs according to any one of above [1] to [36], [48], and [59] to [83], wherein the composition comprises the component (X) and the component (Y); the pH of the composition at 25° C. is 8.3 or more and 12.5 or less; the mass ratio of the content of the component (X) to the content of the component (Y), (X)/(Y), is 0.005 or more and 150 or less; the total content of the component (X) and the component (Y) in the composition is 1.0 mass % or more and 25 mass % or less.

[85] The method for removing keratotic plugs or the use of a composition for removing keratotic plugs according to any one of above [1] to [36], [48], and [59] to [84], wherein the composition comprises (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol and (Y) one or more basic substances selected from the group consisting of arginine, monoethanolamine, triethanolamine, and morpholine; the mass ratio of the content of the component (X) to the content of the component (Y), (X)/(Y), is 0.008 or more and 120 or less; the pH of the composition at 25° C. is 8.3 or more and 12.5 or less; and the total content of the component (X) and the component (Y) in the component is 2 mass % or more and 15 mass % or less.

[86] The method for removing keratotic plugs or the use of a composition for removing keratotic plugs according to any one of above [1] to [36], [48], and [59] to [85], wherein the composition comprises (X) one or more selected from the group consisting of (X1) 2-amino-2-hydroxymethyl-1,3-propanediol, (X2) 2-amino-2-methyl-1-propanol, and (X3) 2-amino-2-methyl-1,3-propanediol and (Y) one or more basic substances selected from the group consisting of arginine, monoethanolamine, triethanolamine, and morpholine; the mass ratio of the content of the component (X) to the content of the component (Y), (X)/(Y), is 0.01 or more and 100 or less; the pH of the composition at 25° C. is; and the total content of the component (X) and the component (Y) in the composition is 5 mass % or more and 12 mass % or less.

[87] The method for removing keratotic plugs or the use of a composition for removing keratotic plugs according to any one of above [1] to [36], [48], and [59] to [85], wherein the composition comprises and (Y) one or two basic substances selected from the group consisting of arginine and triethanolamine; the mass ratio of the content of the component (X) to the content of the component (Y), (X)/(Y), is 0.01 or more and 100 or less; the pH of the composition at 25° C. is or less; the total content of the component (X) and the component (Y) in the composition is 5 mass % or more and 12 mass % or less.

EXAMPLES

The present invention will now be specifically described based on Examples. Unless otherwise indicated in the table, the content of each component is represented by "mass %" (only sodium cocoyl glutamate as the component (A1) is shown in terms of acid equivalent).

Samples were prepared according to the prescriptions shown in Tables 1 to 19. Specifically, each sample can be prepared by heating water to 70° C. in advance, sequentially adding all remaining components to the water, mixing them by stirring, and cooling the resulting mixture to 20° C. Tables 1 to 19 also show the results. The pH of each of the resulting samples was measured at 25° C. with a pH meter (manufactured by HORIBA, Ltd., Model No. F-22).

<<Evaluation of Detergency Against Keratotic Plugs>>

1. Evaluation of Detergency Against Keratotic Plugs During Cleansing

Keratotic plugs in the nasal region were removed with "Biore Nose Pack (manufactured by Kao Corporation)", the resulting keratotic plugs on the pack were gently taken out with tweezers.

The resulting keratotic plugs were placed on a slide glass and were covered with a cover glass, and 0.05 mL of a sample was dropwise added to an edge of the cover glass. Consequently, the sample entered into the gap between the slide glass and the cover glass by capillary phenomenon and was brought into contact with the keratotic plugs. The contact of the keratotic plugs with the sample was recorded with a digital microscope (VHX-5000, manufactured by Keyence Corporation, magnification: ×150), and the penetration of the sample into the keratotic plugs and the collapse state of the keratotic plugs were evaluated after one minute from the contact of the keratotic plugs with the sample. The results of each evaluation are shown in the columns "Detergency against keratotic plugs (penetration)" and "Detergency against keratotic plugs (during cleansing)" in Tables. The measurements were performed at 25° C.

The penetration was relatively evaluated by 11 criteria from the state 1 "the sample hardly penetrated into the keratotic plug" to the state 11 "the sample penetrated to the center of the keratotic plug". The collapsibility by the detergency against keratotic plugs was relatively evaluated by 11 criteria from the state 1 "almost no change is observed in the external appearance of the keratotic plug" to the state 11 "peeling or separation is observed in the area from the surface layer to the central portion of the keratotic plug (the initial appearance of the keratotic plug is not retained)".

2. Evaluation of Detergency Against Keratotic Plugs after Washing with Water

After one minute from the contact of the keratotic plugs with the sample, KimWipes (registered trademark) was brought into contact with an edge of the cover glass to remove the sample under the cover glass. Subsequently, 0.05 mL of water was dropwise added to an edge of the cover glass. The sample dropwise added with water was recorded with the digital microscope, and the collapse state of the keratotic plugs was evaluated after one minute from the contact of the keratotic plugs with water according to the criteria for evaluating collapsibility of the keratotic plugs. The results of the evaluation are shown in the column "Detergency against keratotic plugs (after washing with water)" in Table. The measurements were performed at 25° C.

<<Evaluation of Effect of Suppressing Protein Aggregation>>

Thirty milliliters of a sample and 0.06 g of an insoluble protein (zein protein) were placed in a 35-mL standard glass bottle, and the concentration of the insoluble protein was adjusted to 0.2 mass % (test sample). Separately, a standard sample was prepared by using water instead of the sample and adjusting the concentration of the insoluble protein to 0.2 mass %. Subsequently, the standard glass bottles were sufficiently shaken and stirred up and down (shake width: 15 cm, 20 times at a shake rate of 5 times per 3 seconds) in a thermostatic chamber of 25° C. and were left to stand for 3 minutes. The precipitation state of the insoluble protein was then visually verified, and the ratio of the amount of the precipitated standard sample to the amount of the precipitated test sample (the height of the precipitate in each standard glass bottle was measured as the precipitation amount), (precipitation amount of standard sample)/(precipitation amount of test sample), was calculated. A higher ratio indicates a higher effect of suppressing protein aggregation.

<<Evaluation of Skin Irritation>>

Two expert panelists dropwise applied 0.1 mL of each sample to the palm and massaged the palm for 10 seconds. The sliminess of the skin during the massage was evaluated according to the following criteria. The results of evaluation are each expressed by the average of the results evaluated by the two expert panelists. Higher sliminess indicates higher dissolution of the horny layer and higher skin irritation.

(Criteria)

3: Sense of strong sliminess
2: Sense of slight sliminess
1: No sense of sliminess <<Evaluation of Softness of Skin>>

Two expert panelists uniformly applied 1 mL of each sample to the face and massaged the face with hands for 30 seconds. Subsequently, the face was rinsed with tap water (amount of rinse water: 1000 mL per 10 seconds, water temperature: 25° C. to 30° C.) for 30 seconds. After the rinsing, the moisture was wiped off with a towel, and the softness of the skin after 20 minutes was evaluated according to the following criteria. The results of evaluation are each expressed by the average of the results evaluated by the two expert panelists.

The sample causing skin irritation when applied was not subjected to the test for evaluating softening the skin. The sample not subjected to the evaluation is indicated by "-" in the column of the result of evaluation.

(Criteria)

4: Very soft
3: Slightly soft
2: Slightly stretched
1: Very stretched

<<Evaluation of Foaming Property>>

Two expert panelists dropwise applied 1 mL of each sample onto a previously wetted hand and rubbed the palms of both hands for 10 seconds to foam the sample. The state of the foam was evaluated according to the following criteria. The results of evaluation are each expressed by the average of the results evaluated by the two expert panelists.

(Criteria)

4: Highly foamed
3: Moderately foamed
2: Slightly foamed
1: Hardly foamed
0: Not foamed <<Evaluation of Sebum Cleansing Ability>>

Carbon black was dispersed in an amount of 5 mass % in 95 mass % of the model sebum shown below for coloring, and the dispersion was melted at 50° C. and then applied to in a size of 3 cm in diameter (application quantity of model sebum: about 0.26 mg/cm$^2$). After the application, the model sebum was left to stand for 15 minutes to dry, and 1.0 mL of a sample was applied thereon, followed by massage for 30 seconds. The application site was rinsed with tap water (amount of rinse water: 1000 mL per 10 seconds, water temperature: 25° C. to 30° C.) for 30 seconds. The amount of the model sebum remaining on the skin after the rinsing was visually verified, and the sebum cleansing ability was evaluated according to the following criteria.

(Model Sebum)

| Component | mass % |
|---|---|
| Squalene | 9.0 |
| Myristyl myristate | 24.9 |
| Cotton seed oil | 47.0 |
| Cholesterol | 2.0 |
| Cholesteryl palmitate | 2.0 |
| Lauric acid | 0.2 |
| Myristic acid | 2.5 |
| Palmitic acid | 6.0 |
| Stearic acid | 0.9 |
| Oleic acid | 6.4 |
| Total | 100 |

(Criteria)

5: The boundary between the model sebum-application site and the non-application site is not observed at all.
4: A part of the boundary between the model sebum-application site and the non-application site is slightly observed.
3: The entire boundary between the model sebum-application site and the non-application site is very faintly observed.
2: The entire boundary between the model sebum-application site and the non-application site is faintly observed.
1: The entire boundary between the model sebum-application site and the non-application site is clearly observed.

<<Evaluation of Makeup Removability>>

A foundation (SOFINA Primavista (registered trademark) liquid foundation ochre 05, manufactured by Kao Corporation) was uniformly applied to the inside of a in a size of 3 cm in diameter and was dried for 15 minutes. Onto the foundation-application site, 1.0 mL of a sample was applied, followed by massage for 30 seconds. The application site was rinsed with tap water (amount of rinse water: 1000 mL per 10 seconds, water temperature: 25° C. to 30° C.) for 30 seconds. The amount of the foundation remaining on the skin after the rinsing was visually verified for evaluation according to the following criteria.

(Criteria)
5: The boundary between the foundation-application site and the non-application site is not observed at all.
4: A part of the boundary between the foundation-application site and the non-application site is slightly observed.
3: The entire boundary between the foundation application site and the non-application site is very faintly observed.
2: The entire boundary between the foundation application site and the non-application site is faintly observed.
1: The entire boundary between the foundation application site and the non-application site is clearly observed.

TABLE 1

| | | | Test Example x1-1 | Test Example x2-1 | Test Example x3-1 | Test Example r-1 | Test Example r-2 | Test Example r-3 | Test Example r-4 |
|---|---|---|---|---|---|---|---|---|---|
| (X) | (X1) | Tris | 5 | | | | | | |
| | (X2) | AMP | | 5 | | | | | |
| | (X3) | AMPD | | | 5 | | | | |
| | | POE (2) Na lauryl sulfate*[1] | | | | 5 | | | |
| | | Disodium hydrogen phosphate | | | | | 5 | | |
| | | Trisodium phosphate | | | | | | 5 | |
| | | Sodium hydrogen carbonate | | | | | | | 5 |
| | | 1 M Hydrochloric acid | 0.92 | 20 | 4.33 | | | 15 | |
| | | 1 M Sodium hydroxide | | | | | 0.3 | | 24 |
| | | Water (making up the balance) | 94.08 | 75 | 90.67 | 95 | 94.7 | 80 | 71 |
| | | Total | 100 | 100 | 100 | 100 | 100 | 100 | 100 |
| | | pH | 10 | 10 | 10 | 10 | 9.8 | 9.6 | 9.4 |
| Keratotic plug detergency (penetration) | | | 9 | 5 | 5 | 1 | 2 | 1 | 2 |
| Keratotic plug detergency (during cleansing) | | | 9 | 5 | 5 | 1 | 2 | 1 | 2 |
| Keratotic plug detergency (after washing with water) | | | 11 | 8 | 8 | 1 | 2 | 1 | 2 |
| Protein aggregation-suppressing effect | | | 10 | 10 | 10 | unmeasurable (dissolution) | 10 | 3 | 2.5 |

Furthermore, the action on proteins was strong to dissolve the proteins.

Accordingly, the collapse of the keratotic plugs did not progress even when keratotic plugs were in contact with disodium hydrogen phosphate, trisodium phosphate, or sodium hydrogen carbonate. The detergency against keratotic plugs was hardly expressed.

Furthermore, were brought into contact with water, and the collapse of the keratotic plugs did not progress.

Accordingly, in order to accelerate the collapse of keratotic plugs during washing with water and to remove keratotic plugs from pores,

TABLE 2

| | | | Test Example x1-1 | Test Example x1-2 | Test Example x1-3 | Test Example x1-4 | Test Example x1-5 | Test Example x1-6 |
|---|---|---|---|---|---|---|---|---|
| (X) | (XI) | Tris | 5 | 0.1 | 0.5 | 1 | 10 | 20 |
| | | 1 M Hydrochloric acid | 0.92 | 0.02 | 0.92 | 0.18 | 1.83 | 3.67 |
| | | 1 M Sodium hydroxide | | | | | | |
| | | Water (making up the balance) | 94.08 | 99.88 | 98.58 | 98.82 | 88.17 | 76.33 |
| | | Total | 100 | 100 | 100 | 100 | 100 | 100 |
| | | PH | 10 | 10 | 10 | 10 | 10 | 10 |

TABLE 2-continued

| | | | | | | |
|---|---|---|---|---|---|---|
| Keratotic plug detergency (during cleansing) | 9 | 3 | 4 | 5 | 9 | 5 |
| Skin irritation | 1 | 1 | 1 | 1 | 1 | 1 |

| | | | Test Example x1-7 | Test Example x1-8 | Test Example x1-9 | Test Example x1-10 | Test Example x1-11 | Test Example x1-12 |
|---|---|---|---|---|---|---|---|---|
| (X) | (XI) | Tris | 30 | 5 | 5 | 5 | 10 | 5 |
| | | 1 M Hydrochloric acid | 5.5 | 4 | | | | |
| | | 1 M Sodium hydroxide | | | | 1 | 1.8 | 12.8 |
| | | Water (making up the balance) | 64.5 | 91 | 95 | 94 | 88.2 | 82.2 |
| | | Total | 100 | 100 | 100 | 100 | 100 | 100 |
| | | pH | 10 | 9 | 11 | 12 | 12 | 13 |
| Keratotic plug detergency (during cleansing) | | | 3 | 5 | 9 | 11 | 11 | 11 |
| Skin irritation | | | 1 | 1 | 1 | 2 | 2 | 3 |

TABLE 3

| | | | Test Example x2-1 | Test Example x2-2 | Test Example x2-3 | Test Example x2-4 | Test Example x2-5 | Test Example x2-6 |
|---|---|---|---|---|---|---|---|---|
| (X) | (X2) | AMP | 5 | 0.5 | 1 | 10 | 20 | 30 |
| | | 1 M Hydrochloric acid | 20 | 2 | 4 | 40 | 80 | 70 |
| | | 1 M Sodium hydroxide | | | | | | |
| | | Water (making up the balance) | 75 | 97.5 | 95 | 50 | | |
| | | Total | 100 | 100 | 100 | 100 | 100 | 100 |
| | | pH | 10 | 10 | 10 | 10 | 9.8 | 10 |
| Keratotic plug detergency (during cleansing) | | | 5 | 3 | 4 | 5 | 5 | 3 |
| Skin irritation | | | 1 | 1 | 1 | 1 | 1 | 1 |

| | | | Test Example x2-7 | Test Example x2-8 | Test Example x2-9 | Test Example x2-10 | Test Example x2-11 |
|---|---|---|---|---|---|---|---|
| (X) | (X2) | AMP | 5 | 5 | 5 | 10 | 5 |
| | | 1 M Hydrochloric acid | 49 | 16 | 20 | 40 | |
| | | 1 M Sodium hydroxide | | | | | 12 |
| | | Water (making up the balance) | 46 | 79 | 75 | 50 | 83 |
| | | Total | 100 | 100 | 100 | 100 | 100 |
| | | pH | 9 | 11 | 11.9 | 12 | 12.9 |
| Keratotic plug detergency (during cleansing) | | | 3 | 7 | 9 | 11 | 11 |
| Skin irritation | | | 1 | 1 | 2 | 2 | 3 |

TABLE 4

| | | | Test Example x3-1 | Test Example x3-2 | Test Example x3-3 | Test Example x3-4 | Test Example x3-5 | Test Example x3-6 | Test Example x3-7 | Test Example x3-8 | Test Example x3-9 | Test Example x3-10 | Test Example x3-11 |
|---|---|---|---|---|---|---|---|---|---|---|---|---|---|
| (X) | (X3) | AMPD | 5 | 0.5 | 1 | 10 | 20 | 30 | 5 | 5 | 5 | 10 | 5 |
| | | 1M Hydrochloric acid | 4.33 | 0.43 | 0.87 | 8.67 | 17.33 | 26 | 13 | | | | |

TABLE 4-continued

|  | Test Example x3-1 | Test Example x3-2 | Test Example x3-3 | Test Example x3-4 | Test Example x3-5 | Test Example x3-6 | Test Example x3-7 | Test Example x3-8 | Test Example x3-9 | Test Example x3-10 | Test Example x3-11 |
|---|---|---|---|---|---|---|---|---|---|---|---|
| 1M Sodium hydroxide |  |  |  |  |  |  |  |  | 2 | 1 | 6 |
| Water (making up the balance) | 90.67 | 99.07 | 98.13 | 81.33 | 62.67 | 44 | 82 | 82 | 93 | 89 | 89 |
| Total | 100 | 100 | 100 | 100 | 100 | 100 | 100 | 100 | 100 | 100 | 100 |
| pH | 10 | 10 | 10 | 10 | 10 | 10 | 9.1 | 11 | 12 | 12 | 13 |
| Keratotic plug detergency (during cleansing) | 5 | 3 | 4 | 5 | 3 | 3 | 3 | 7 | 9 | 9 | 9 |
| Skin irritation | 1 | 1 | 1 | 1 | 1 | 1 | 1 | 1 | 2 | 2 | 3 |

TABLE 5

|  |  |  | Test Example xx-1 | Test Example xx-2 | Test Example xx-3 | Test Example xx-4 | Test Example xx-5 | Test Example xx-6 | Test Example xx-7 | Test Example xx-8 | Test Example xx-9 | Test Example xx-10 |
|---|---|---|---|---|---|---|---|---|---|---|---|---|
| (X) | (X1) | Tris | 5 | 5 |  | 1 | 9 | 1 |  | 9 |  | 5 |
|  | (X2) | AMP | 5 |  | 5 | 5 | 9 | 1 |  |  | 9 | 1 | 5 |
|  | (X3) | AMPD |  | 5 | 5 |  |  | 9 | 1 | 1 | 9 | 5 |
|  |  | 1M Hydrochloric acid | 20.915 | 5.3 | 24.3 | 36.2 | 5.6 | 7.983 | 2.4 | 36.87 | 11.6 | 18 |
|  |  | 1M Sodium hydroxide |  |  |  |  |  |  |  |  |  |  |
|  |  | Water (making up the balance) | 69.085 | 84.7 | 65.7 | 53.8 | 84.4 | 82.017 | 87.6 | 53.13 | 78.4 | 67 |
|  |  | Total | 100 | 100 | 100 | 100 | 100 | 100 | 100 | 100 | 100 | 100 |
|  |  | pH | 10 | 10 | 10 | 10 | 10 | 10 | 10 | 10 | 10 | 10 |
| Keratotic plug detergency (during cleansing) |  |  | 9 | 10 | 7 | 5 | 9 | 9 | 11 | 3 | 5 | 10 |

TABLE 6

|  |  |  | Test Example xy-1 | Test Example xy-2 | Test Example xy-3 | Test Example xy-4 | Test Example xy-5 | Test Example xy-6 | Test Example xy-7 | Test Example xy-8 | Test Example xy-9 |
|---|---|---|---|---|---|---|---|---|---|---|---|
| (X) | (X1) | Tris | 0.1 | 0.1 | 0.1 | 0.1 | 10 |  |  |  |  |
|  | (X2) | AMP |  |  |  |  |  | 0.1 | 0.1 | 0.1 | 0.1 |
|  | (X3) | AMPD |  |  |  |  |  |  |  |  |  |
| (Y) |  | Arginine | 10 |  |  |  | 0.1 | 10 |  |  |  |
|  |  | Triethanolamine |  | 10 |  |  |  |  | 10 |  |  |
|  |  | Monoethanolamine |  |  | 10 |  |  |  |  | 10 |  |
|  |  | Morpholine |  |  |  | 10 |  |  |  |  | 10 |
|  |  | 1M Hydrochloric acid | 6.2 | 1 | 40 | 9 | 1 | 5 | 0.5 | 40 | 2 |
|  |  | 1M Sodium hydroxide |  |  |  |  |  |  |  |  |  |
|  |  | Water (making up the balance) | 83.7 | 88.9 | 49.9 | 87.9 | 88.9 | 84.9 | 89.4 | 49.9 | 87.9 |
|  |  | Total | 100 | 100 | 100 | 100 | 100 | 100 | 100 | 100 | 100 |
|  |  | pH | 10.1 | 9.7 | 10.1 | 10 | 10.1 | 10.1 | 10 | 10.1 | 10.1 |
|  |  | (X)/(Y) | 0.01 | 0.01 | 0.01 | 0.01 | 100 | 0.01 | 0.01 | 0.01 | 0.01 |
| Keratotic plug detergency (during cleansing) |  |  | 9 | 9 | 7 | 9 | 9 | 7 | 7 | 6 | 7 |
| Softness of skin |  |  | 3 | 3 | — | — | 3 | 3 | 3 | — | — |

TABLE 7

|  |  |  | Test Example xy-10 | Test Example xy-11 | Test Example xy-12 | Test Example xy-13 | Test Example xy-14 | Test Example xy-15 | Test Example xy-16 |
|---|---|---|---|---|---|---|---|---|---|
| (X) | (X1) | Tris |  |  |  |  | 5 | 5 | 5 |
|  | (X2) | AMP |  |  |  |  |  |  |  |
|  | (X3) | AMPD | 0.1 | 0.1 | 0.1 | 0.1 |  |  |  |

TABLE 7-continued

|   |   |   |   |   |   |   |   |   |   |
|---|---|---|---|---|---|---|---|---|---|
| (Y) |   | Arginine | 10 |  |  |  | 5 | 5 | 5 |
|   |   | Triethanolamine |  | 10 |  |  |  |  |  |
|   |   | Monoethanolamine |  |  | 10 |  |  |  |  |
|   |   | Morpholine |  |  |  | 10 |  |  |  |
|   |   | 1M Hydrochloric acid | 5 | 0.8 | 40 | 4 | 40 | 19 | 3.4 |
|   |   | 1M Sodium hydroxide |  |  |  |  |  |  |  |
|   |   | Water (making up the balance) | 84.9 | 89.9 | 49.9 | 85.9 | 50 | 71 | 86.6 |
|   |   | Total | 100 | 100 | 100 | 100 | 100 | 100 | 100 |
|   |   | pH | 10.1 | 10 | 10.1 | 10 | 8.3 | 9.1 | 10 |
|   |   | (X)/(Y) | 0.01 | 0.01 | 0.01 | 0.01 | 1 | 1 | 1 |
|   |   | Keratotic plug detergency (during cleansing) | 5 | 10 | 9 | 7 | 4 | 7 | 9 |
|   |   | Softness of skin | 3 | 3 | — | — | 3 | 3 | 3 |

|   |   |   | Test Example xy-17 | Test Example xy-18 | Test Example xy-19 | Test Example xy-20 | Test Example xy-21 | Test Example x1-1 | Test Example x1-5 |
|---|---|---|---|---|---|---|---|---|---|
| (X) | (X1) | Tris | 5 |  |  |  |  | 5 | 10 |
|   | (X2) | AMP |  | 5 | 5 |  |  |  |  |
|   | (X3) | AMPD |  |  |  | 5 | 5 |  |  |
| (Y) |   | Arginine | 5 | 5 | 5 | 5 | 5 |  |  |
|   |   | Triethanolamine |  |  |  |  |  |  |  |
|   |   | Monoethanolamine |  |  |  |  |  |  |  |
|   |   | Morpholine |  |  |  |  |  |  |  |
|   |   | 1M Hydrochloric acid |  | 50 | 26 | 30 | 16 | 0.92 | 1.83 |
|   |   | 1M Sodium hydroxide | 1.6 |  |  |  |  |  |  |
|   |   | Water (making up the balance) | 88.4 | 40 | 64 | 60 | 74 |  |  |
|   |   | Total | 100 | 100 | 100 | 100 | 100 | 100 | 100 |
|   |   | pH | 12 | 9.1 | 10.1 | 9.1 | 10.1 | 10 | 10 |
|   |   | (X)/(Y) | 1 | 1 | 1 | 1 | 1 | 10 | 10 |
|   |   | Keratotic plug detergency (during cleansing) | 11 | 6 | 7 | 6 | 6 | 9 | 9 |
|   |   | Softness of skin | 3 | 3 | 3 | 3 | 3 | 2.5 | 3 |

TABLE 8

|   |   |   | Test Example xa1-1 | Test Example xa1-2 | Test Example xa1-3 | Test Example xa1-4 | Test Example xa1-5 | Test Example xa1-6 | Test Example xa1-7 | Test Example xa1-8 | Test Example xa1-9 |
|---|---|---|---|---|---|---|---|---|---|---|---|
| (X) | (X1) | Tris | 5 | 5 | 5 | 5 | 0.5 | 0.5 | 25 | 5 | 5 |
|   | (X2) | AMP |  |  |  |  |  |  |  |  |  |
|   | (X3) | AMPD |  |  |  |  |  |  |  |  |  |
| (A) | (A1) | Lauric acid | 0.5 |  |  |  | 0.5 | 3 | 0.5 | 0.1 | 3 |
|   |   | Fatty acid mixture[*2] |  | 0.6 |  |  |  |  |  |  |  |
|   |   | Na cocoyl glutamate |  |  | 0.5 |  |  |  |  |  |  |
|   |   | POE (4.5) lauryl ether acetate[*3] |  |  |  | 0.5 |  |  |  |  |  |
|   |   | 1M Hydrochloric acid |  |  | 0.4 |  |  |  |  |  |  |
|   |   | 1M Sodium hydroxide | 2 | 1 |  |  | 3 | 7.2 |  |  | 12 |
|   |   | Water (making up the balance) | 92.5 | 93.4 | 94.1 | 94.5 | 96 | 96 | 74.5 | 94.9 | 80 |
|   |   | Total | 100 | 100 | 100 | 100 | 100 | 100 | 100 | 100 | 100 |
|   |   | pH | 10 | 10 | 10 | 10 | 10 | 10 | 10.1 | 10 | 10 |
|   |   | (X)/(A1) | 10.00 | 8.33 | 10.00 | 10.00 | 1.00 | 0.17 | 50.00 | 50.00 | 1.67 |
|   |   | Keratotic plug detergency (during cleansing) | 10 | 10 | 9 | 10 | 7 | 4 | 3 | 7 | 5 |
|   |   | Foaming property | 2 | 2 | 1.5 | 3 | 2 | 1.5 | 3 | 1.5 | 1.5 |

TABLE 9

| | | | Test Example xa1-10 | Test Example xa1-11 | Test Example xa1-12 | Test Example xa1-13 | Test Example xa1-14 | Test Example xa1-15 | Test Example xa1-16 | Test Example xa1-17 |
|---|---|---|---|---|---|---|---|---|---|---|
| (X) | (X1) | Tris | | | | | | | | |
| | (X2) | AMP | 5 | 5 | 5 | 5 | 0.5 | 25 | 5 | 5 |
| | (X3) | AMPD | | | | | | | | |
| (A) | (A1) | Lauric acid | 0.5 | | | | 0.5 | 0.5 | 0.1 | 3 |
| | | Fatty acid mixture*2 | | 0.6 | | | | | | |
| | | Na cocoyl glutamate | | | 0.5 | | | | | |
| | | POE (4.5) lauryl ether acetate*3 | | | | 0.5 | | | | |
| | | 1M Hydrochloric acid | 16 | 16 | 18 | 18 | 1 | 40 | 18 | 10 |
| | | 1M Sodium hydroxide | | | | | | | | |
| | | Water (making up the balance) | 78.5 | 78.4 | 76.5 | 76.5 | 98 | 34.5 | 76.9 | 82 |
| | | Total | 100 | 100 | 100 | 100 | 100 | 100 | 100 | 100 |
| | | pH | 10 | 10 | 10.1 | 10.1 | 10 | 10 | 10 | 10 |
| | | (X)/(A1) | 10.00 | 8.33 | 10.00 | 10.00 | 1.00 | 50.00 | 50.00 | 1.67 |
| | | Keratotic plug detergency (during cleansing) | 5 | 7 | 9 | 7 | 5 | 5 | 5 | 5 |
| | | Foaming property | 2 | 2 | 1.5 | 3 | 2 | 3 | 1.5 | 1.5 |

TABLE 10

| | | | Test Example xa1-18 | Test Example xa1-19 | Test Example xa1-20 | Test Example xa1-21 | Test Example xa1-22 | Test Example xa1-23 | Test Example xa1-24 | Test Example xa1-25 | Test Example x1-1 | Test Example x2-1 | Test Example x3-1 |
|---|---|---|---|---|---|---|---|---|---|---|---|---|---|
| (X) | (X1) | Tris | | | | | | | | | 5 | | |
| | (X2) | AMP | | | | | | | | | | 5 | |
| | (X3) | AMPD | 5 | 5 | 5 | 5 | 0.5 | 25 | 5 | 5 | | | 5 |
| (A) | (A1) | Lauric acid | 0.5 | | | | 0.5 | 0.5 | 0.1 | 3 | | | |
| | | Fatty acid mixture*2 | | 0.6 | | | | | | | | | |
| | | Na cocoyl glutamate | | | 0.5 | | | | | | | | |
| | | POE (4.5) lauryl ether acetate*3 | | | | 0.5 | | | | | | | |
| | | 1M Hydrochloric acid | 2 | 2 | 3 | 2 | | | | | | | |
| | | 1M Sodium hydroxide | | | | | 2 | 14 | 2 | | 0.92 | 20 | 4.33 |
| | | Water (making up the balance) | 92.5 | 92.4 | 91.5 | 92.5 | 97 | 60.5 | 92.9 | 92 | 94.08 | 75 | 90.67 |
| | | Total | 100 | 100 | 100 | 100 | 100 | 100 | 100 | 100 | 100 | 100 | 100 |
| | | pH | 10 | 10.1 | 10 | 10 | 10 | 10 | 10 | 10 | 10 | 10 | 10 |
| | | (X)/(A1) | 10.00 | 8.33 | 10.00 | 10.00 | 1.00 | 50.00 | 50.00 | 1.67 | — | — | — |
| | | Keratotic plug detergency (during cleansing) | 7 | 7 | 7 | 7 | 5 | 7 | 7 | 5 | 9 | 5 | 5 |
| | | Foaming property | 2 | 2 | 1.5 | 3 | 2 | 3 | 1.5 | 1.5 | 0 | 0 | 0 |

TABLE 11

| | | | Test Example xa2-1 | Test Example xa2-2 | Test Example xa2-3 | Test Example xa2-4 | Test Example xa2-5 | Test Example xa2-6 | Test Example xa2-7 | Test Example xa2-8 | Test Example xa2-9 |
|---|---|---|---|---|---|---|---|---|---|---|---|
| (X) | (X1) | Tris | 1 | 1 | 1 | 0.5 | 25 | 5 | 5 | 5 | 0.1 |
| | (X2) | AMP | | | | | | | | | |
| | (X3) | AMPD | | | | | | | | | |
| (A) | (A2) | POE (2) Na lauryl sulfate*1 | 2 | | | 2 | 2 | 0.1 | 0.5 | 5 | 15 |
| | | Na lauryl sulfate*4 | | 2 | | | | | | | |
| | | IOS*5 | | | 2 | | | | | | |
| | | 1M Hydrochloric acid | 1.2 | 1.2 | 1 | 0.14 | 4 | 0.6 | 0.8 | 1.6 | |
| | | 1M Sodium hydroxide | | | | | | | | | |

TABLE 11-continued

|  | Test Example xa2-1 | Test Example xa2-2 | Test Example xa2-3 | Test Example xa2-4 | Test Example xa2-5 | Test Example xa2-6 | Test Example xa2-7 | Test Example xa2-8 | Test Example xa2-9 |
|---|---|---|---|---|---|---|---|---|---|
| Water (making up the balance) | 95.8 | 95.8 | 96 | 97.36 | 69 | 94.3 | 93.7 | 88.4 | 84.9 |
| Total | 100 | 100 | 100 | 100 | 100 | 100 | 100 | 100 | 100 |
| pH | 10 | 10.1 | 10.1 | 10 | 10.1 | 10 | 10 | 10 | 10 |
| (X)/(A2) | 0.50 | 0.50 | 0.50 | 0.25 | 12.50 | 50.00 | 10.00 | 1.00 | 0.01 |
| Keratotic plug detergency (during cleansing) | 7 | 7 | 9 | 5 | 7 | 9 | 10 | 9 | 3 |
| Foaming property | 3 | 4 | 2 | 2 | 2 | 2 | 2.5 | 3 | 3.5 |

TABLE 12

|  |  |  | Test Example xa2-10 | Test Example xa2-11 | Test Example xa2-12 | Test Example xa2-13 | Test Example xa2-14 | Test Example xa2-15 | Test Example xa2-16 | Test Example xa2-17 | Test Example xa2-18 |
|---|---|---|---|---|---|---|---|---|---|---|---|
| (X) | (X1) | Tris | | | | | | | | | |
|  | (X2) | AMP | 5 | 5 | 5 | 0.5 | 25 | 5 | 5 | 5 | 0.1 |
|  | (X3) | AMPD | | | | | | | | | |
| (A) | (A2) | POE (2) Na lauryl sulfate*1 | 2 | | | 2 | 2 | 0.1 | 0.5 | 5 | 15 |
|  |  | Na lauryl sulfate*4 | | 2 | | | | | | | |
|  |  | IOS*5 | | | 2 | | | | | | |
|  |  | 1M Hydrochloric acid | 18 | 20 | 20 | 2.4 | | 18 | 20 | 22 | 0.2 |
|  |  | 1M Sodium hydroxide | | | | | | | | | |
|  |  | Water (making up the balance) | 75 | 73 | 73 | 95.1 | 73 | 76.9 | 74.5 | 68 | 84.7 |
|  |  | Total | 100 | 100 | 100 | 100 | 100 | 100 | 100 | 100 | 100 |
|  |  | pH | 10.1 | 10 | 10 | 10 | 10.2 | 10 | 10 | 10 | 10.3 |
|  |  | (X)/(A2) | 2.50 | 2.50 | 2.50 | 0.25 | 12.50 | 50.00 | 10.00 | 1.00 | 0.01 |
|  |  | Keratotic plug detergency (during cleansing) | 9 | 9 | 9 | 5 | 7 | 7 | 9 | 7 | 3 |
|  |  | Foaming property | 3 | 4 | 2 | 2 | 2 | 2 | 2.5 | 3 | 3.5 |

TABLE 13

|  |  |  | Test Example xa2-19 | Test Example xa2-20 | Test Example xa2-21 | Test Example xa2-22 | Test Example xa2-23 | Test Example xa2-24 | Test Example xa2-25 | Test Example xa2-26 | Test Example xa2-27 | Test Example xa2-28 | Test Example x1-1 | Test Example x2-1 | Test Example x3-1 |
|---|---|---|---|---|---|---|---|---|---|---|---|---|---|---|---|
| (X) | (X1) | Tris | | | | | | | | | | | 1 | | |
|  | (X2) | AMP | | | | | | | | | | | | 1 | |
|  | (X3) | AMPD | 5 | 5 | 5 | 0.5 | 25 | 5 | 5 | 5 | 5 | 0.1 | | | 1 |
| (A) | (A2) | POE (2) Na lauryl sulfate*1 | 2 | | | 2 | 2 | 0.1 | 0.5 | 5 | 10 | 15 | | | |
|  |  | Na lauryl sulfate*4 | | 2 | | | | | | | | | | | |
|  |  | IOS*5 | | | 2 | | | | | | | | | | |
|  |  | 1M Hydrochloric acid | 5 | 5.2 | 4.4 | 1 | 15 | 4 | 4 | 5 | 1.5 | | 0.18 | 4 | 0.18 |
|  |  | 1M Sodium hydroxide | | | | | | | | | | | | | |
|  |  | Water (making up the balance) | 88 | 87.8 | 88.6 | 96.5 | 58 | 90.9 | 90.5 | 85 | 83.5 | 84.9 | 98.82 | 95 | 98.82 |
|  |  | Total | 100 | 100 | 100 | 100 | 100 | 100 | 100 | 100 | 100 | 100 | 100 | 100 | 100 |
|  |  | pH | 10 | 10.1 | 10.1 | 9.8 | 10.2 | 10 | 10 | 10 | 10.3 | 10.2 | 10 | 10 | 10 |
|  |  | (X)/(A2) | 2.50 | 2.50 | 2.50 | 0.25 | 12.50 | 50.00 | 10.00 | 1.00 | 0.50 | 0.01 | — | — | — |
|  |  | Keratotic plug detergency (during cleansing) | 9 | 7 | 9 | 7 | 7 | 7 | 7 | 9 | 10 | 3 | 5 | 4 | 4 |
|  |  | Foaming property | 3 | 4 | 2 | 2 | 2 | 2 | 2.5 | 3 | 4 | 3.5 | 0 | 0 | 0 |

TABLE 14

|  |  |  | Test Example xb-1 | Test Example xb-2 | Test Example xb-3 | Test Example xb-4 | Test Example xb-5 | Test Example xb-6 | Test Example xb-7 | Test Example xb-8 | Test Example xb-9 | Test Example xb-10 | Test Example xb-11 | Test Example xb-12 |
| --- | --- | --- | --- | --- | --- | --- | --- | --- | --- | --- | --- | --- | --- | --- |
| (X) | (X1) | Tris | 0.5 | 5 | 5 | 0.5 | 5 | 25 | | | | | | |
| | (X2) | AMP | | | | | | | | | 0.5 | 0.5 | 5 | 5 | 5 | 25 |
| | (X3) | AMPD | | | | | | | | | | | | |
| (B) | (B1) | POE (21) lauryl ether (HLB16.6)[*6] | 1 | 0.5 | 1 | | | 1 | 1 | 15 | 0.5 | 1 | | 1 |
| | | Polyethylene glycol monolaurate (12 E.O.) (HLB13.7)[*7] | | | | 15 | 15 | | | | | | 15 | |
| | | 1M Hydrochloric acid | 0.14 | 1 | 1 | | | 4 | 2 | | 20 | 20 | 6 | 74 |
| | | 1M Sodium hydroxide | | | | 0.3 | | | | | | | | |
| | | Water (making up the balance) | 98.36 | 93.5 | 93 | 84.2 | 80 | 70 | 96.5 | 84.5 | 74.5 | 74 | 74 | |
| | | Total | 100 | 100 | 100 | 100 | 100 | 100 | 100 | 100 | 100 | 100 | 100 | 100 |
| | | pH | 10 | 9.8 | 10 | 10.3 | 10 | 10 | 10 | 10.3 | 10 | 10 | 10.3 | 10 |
| | | (X)/(B) | 0.50 | 10.00 | 5.00 | 0.03 | 0.33 | 25.00 | 0.50 | 0.03 | 10.00 | 5.00 | 0.33 | 25.00 |
| | | Keratotic plug detergency (during cleansing) | 5 | 9 | 9 | 6 | 9 | 7 | 7 | 5 | 9 | 7 | 5 | 5 |
| | | Sebum detergency | 4 | 4.5 | 4.5 | 4.5 | 4.5 | 5 | 4 | 4.5 | 4.5 | 4.5 | 4.5 | 5 |

TABLE 15

|  |  |  | Test Example xb-13 | Test Example xb-14 | Test Example xb-15 | Test Example xb-16 | Test Example xb-17 | Test Example x1-3 | Test Example x2-2 | Test Example x3-2 |
| --- | --- | --- | --- | --- | --- | --- | --- | --- | --- | --- |
| (X) | (X1) | Tris | | | | | | 0.5 | | |
| | (X2) | AMP | | | | | | | 0.5 | |
| | (X3) | AMPD | 0.5 | 5 | 5 | 5 | 25 | | | 0.5 |
| (B) | (B1) | POE (21) lauryl ether (HLB16.6)[*6] | 1 | 0.5 | 1 | 5 | 1 | | | |
| | | Polyethylene glycol monolaurate (12 E.O.) (HLB13.7)[*7] | | | | | | | | |
| | | 1M Hydrochloric acid | 0.26 | 4 | 4 | 4 | 14 | 0.92 | 2 | 0.43 |
| | | 1M Sodium hydroxide | | | | | | | | |
| | | Water (making up the balance) | 98.24 | 90.5 | 90 | 86 | 60 | 98.58 | 97.5 | 99.07 |
| | | Total | 100 | 100 | 100 | 100 | 100 | 100 | 100 | 100 |
| | | pH | 10 | 10 | 9.9 | 10 | 10.1 | 10 | 10 | 10 |
| | | (X)/(B) | 0.50 | 10.00 | 5.00 | 1.00 | 25.00 | | | |
| | | Keratotic plug detergency (during cleansing) | 7 | 7 | 9 | 9 | 3 | 4 | 3 | 3 |
| | | Sebum detergency | 4 | 4.5 | 4.5 | 4.5 | 5 | 3 | 3 | 3 |

TABLE 16

|  |  |  | Test Example xb-1 | Test Example xb-25 | Test Example xb-10 | Test Example xb-26 | Test Example xb-19 | Test Example xb-27 |
| --- | --- | --- | --- | --- | --- | --- | --- | --- |
| (X) | (X1) | Tris | 5 | 5 | | | | |
| | (X2) | AMP | | | 5 | 5 | | |
| | (X3) | AMPD | | | | | 5 | 5 |
| (B) | (B1) | POE (21) lauryl ether (HLB16.6)[*6] | 1 | | 1 | | 1 | |
| | | Polyethylene glycol monolaurate (12 E.O.) (HLB13.7)[*7] | | 1 | | 1 | | 1 |
| | | Alkyl glucoside (HLB15.7)[*8] | | 0.1 | | 0.1 | | 0.1 |
| | (B2) | Polyglyceryl-2 isostearate (HLB8.0)[*9] | | 0.1 | | 0.1 | | 0.1 |

TABLE 16-continued

|  | Test Example xb-1 | Test Example xb-25 | Test Example xb-10 | Test Example xb-26 | Test Example xb-19 | Test Example xb-27 |
|---|---|---|---|---|---|---|
| 1M Hydrochloric acid | 1 | 0.8 | 20 | 20 | 4 | 4 |
| Water (making up the balance) | 93 | 93 | 74 | 73.8 | 90 | 89.8 |
| Total | 100 | 100 | 100 | 100 | 100 | 100 |
| pH | 10 | 10 | 10 | 10 | 9.9 | 10 |
| (X)/(B) | 5.00 | 4.17 | 5.00 | 4.17 | 5.00 | 4.17 |
| (B1)/(B2) | — | 11.00 | — | 11.00 | — | 11.00 |
| Keratotic plug detergency (during cleansing) | 9 | 9 | 7 | 9 | 9 | 9 |
| Makeup removability | 2 | 4 | 2 | 4 | 2 | 4 |

TABLE 17

|  |  |  | Test Example xya1-1 | Test Example xya1-2 | Test Example xya1-3 | Test Example xya1-4 | Test Example xya1-5 | Test Example xya1-6 | Test Example xya1-7 | Test Example xya1-8 |
|---|---|---|---|---|---|---|---|---|---|---|
| (X) | (X1) | Iris | 5 | 5 | 5 | 5 | 0.5 | 25 | 5 | 5 |
| (Y) |  | Arginine | 5 | 5 | 5 | 5 | 5 | 5 | 5 | 5 |
| (A) | (A1) | Lauric acid | 0.5 |  |  |  | 0.5 | 0.5 | 0.1 | 3 |
|  |  | Fatty acid mixture[*1] |  | 0.6 |  |  |  |  |  |  |
|  |  | Na cocoyl glutamate |  |  | 0.5 |  |  |  |  |  |
|  |  | POE (4.5) lauryl ether acetate[*2] |  |  |  | 0.5 |  |  |  |  |
|  | (A2) | POE (2) Na lauryl sulfate[*3] |  |  |  |  |  |  |  |  |
|  |  | 1M Hydrochloric acid | 2 | 2 | 3 | 3 | 1 | 4 | 4 | 0 |
|  |  | Water (making up the balance) | 87.5 | 87.4 | 86.5 | 86.5 | 93 | 65.5 | 85.9 | 87 |
|  |  | Total | 100 | 100 | 100 | 100 | 100 | 100 | 100 | 100 |
|  |  | pH | 10 | 10 | 10.1 | 10.1 | 10.1 | 10.1 | 10 | 10 |
|  |  | (X)/(A1) | 10.00 | 8.33 | 10.00 | 10.00 | 1.00 | 50.00 | 50.00 | — |
|  |  | (X)/(A2) | — | — | — | — | — | — | — | 1.67 |
|  |  | Keratotic plug detergency (during cleansing) | 9 | 9 | 9 | 10 | 9 | 3 | 9 | 8 |
|  |  | Foaming property | 2 | 2 | 1.5 | 3 | 2 | 3 | 1.5 | 1.5 |

|  |  |  | Test Example xya1-9 | Test Example xya1-10 | Test Example xya1-11 | Test Example xya1-12 | Test Example xya1-13 | Test Example xya1-14 | Test Example xy-15 |
|---|---|---|---|---|---|---|---|---|---|
| (X) | (X1) | Iris | 0.5 | 25 | 5 | 5 | 5 | 5 | 5 |
| (Y) |  | Arginine | 5 | 5 | 5 | 5 | 5 | 5 | 5 |
| (A) | (A1) | Lauric acid |  |  |  |  |  |  |  |
|  |  | Fatty acid mixture[*1] |  |  |  |  |  |  |  |
|  |  | Na cocoyl glutamate |  |  |  |  |  |  |  |
|  |  | POE (4.5) lauryl ether acetate[*2] |  |  |  |  |  |  |  |
|  | (A2) | POE (2) Na lauryl sulfate[*3] | 2 | 2 | 0.1 | 0.5 | 2 | 5 |  |
|  |  | 1M Hydrochloric acid | 5 | 10 | 3 | 4 | 5 | 6 | 3.4 |
|  |  | Water (making up the balance) | 87.5 | 58 | 86.9 | 85.5 | 83 | 79 | 86.6 |
|  |  | Total | 100 | 100 | 100 | 100 | 100 | 100 | 100 |
|  |  | pH | 10 | 10 | 10 | 10 | 10.1 | 10 | 10 |
|  |  | (X)/(A1) | — | — | — | — | — | — | — |
|  |  | (X)/(A2) | 0.25 | 12.50 | 50.00 | 10.00 | 2.50 | 1.00 | — |
|  |  | Keratotic plug detergency (during cleansing) | 7 | 3 | 9 | 9 | 5 | 10 | 9 |
|  |  | Foaming property | 2 | 2 | 7 | 2.5 | 3 | 3 | 0 |

TABLE 18

|   |   |   | Test Example xyb-1 | Test Example xyb-2 | Test Example xyb-3 | Test Example xyb-4 | Test Example xyb-5 | Test Example xyb-6 | Test Example xy-15 |
|---|---|---|---|---|---|---|---|---|---|
| (X) | (X1) | Tris | 5 | 0.5 | 25 | 5 | 5 | 5 | 5 |
| (Y) |  | Arginine | 5 | 5 | 5 | 5 | 5 | 5 | 5 |
| (B) | (B1) | POE (21) lauryl ether (HLB16.6)*6 | 1 | 1 | 1 | 0.5 |  |  |  |
|  |  | Polyethylene glycol monolaurate (12E.O.) (HLB13.7)*7 |  |  |  |  | 5 | 15 |  |
|  |  | 1M Hydrochloric acid | 4 | 4 | 4 | 3 |  |  | 3.4 |
|  |  | Water (making up the balance) | 85 | 89.5 | 65 | 86.5 | 85 | 75 | 86.6 |
|  |  | Total | 100 | 100 | 100 | 100 | 100 | 100 | 100 |
|  |  | pH | 10 | 9.9 | 10 | 10 | 10 | 10 | 10 |
|  |  | (X)/(B) | 5.00 | 0.50 | 25.00 | 10.00 | 1.00 | 0.33 | 1 |
|  |  | Keratotic plug detergency (during cleansing) | 10 | 8 | 9 | 9 | 9 | 10 | 9 |
|  |  | Sebum cleansing ability | 5 | 4.5 | 5 | 5 | 5 | 5 | 4.5 |

TABLE 19

|   |   |   | Test Example xyb-1 | Test Example xyb-7 |
|---|---|---|---|---|
| (X) | (X1) | Tris | 5 | 5 |
| (Y) |  | Arginine | 5 | 5 |
| (B) | (B1) | POE (21) lauryl ether (HLB16.6)*6 | 1 |  |
|  |  | Polyethylene glycol monolaurate (12 E.O.) (HLB13.7)*7 |  | 1 |
|  |  | Alkyl glucoside (HLB15.7)*8 |  | 0.1 |
|  | (B2) | Polyglyceryl-2 isostearate (HLB8.0)*9 |  | 0.1 |
|  |  | 1M Hydrochloric acid | 4 | 4 |
|  |  | Water (making up the balance) | 85 | 84.8 |
|  |  | Total | 100 | 100 |
|  |  | pH | 10 | 9.9 |
|  |  | (X)/(B) | 5.00 | 4.17 |
|  |  | (B1)/(B2) | — | 11.00 |
|  |  | Keratotic plug detergency (during cleansing) | 10 | 8 |
|  |  | Makeup removability | 2 | 4 |

1: Emal 227 (manufactured by Kao Corporation)
2: Lauric acid/myristic acid/palmitic acid/stearic acid=1/3/1/1 (parts by mass)
3: KAO AKIPO RLM-45CA (manufactured by Kao Corporation)
4: Emal 10PT (manufactured by Kao Corporation)
5: Internal olefin sulfonate composition in Production Example 7 in JP-A-2015-28123
6: Emulgen 121 (manufactured by Kao Corporation)
7: Emanon 1112 (manufactured by Kao Corporation)
8: Mydol 10 (manufactured by Kao Corporation)
9: Cosmol 41V (manufactured by The Nisshin OilliO Group, Ltd.)

Example 2

Facial cleansers shown below were prepared. Specifically, each facial cleanser can be prepared by heating water to 70° C. in advance, sequentially adding all remaining components to the water, mixing them by stirring, and cooling the resulting mixture to 25° C.

The following facial cleansers were evaluated for the detergency against keratotic plugs (during cleansing) and the effect of improving the skin color brightness.

<<Evaluation of Effect of Improving Skin Color Brightness>>

Nine expert panelists (male) used the following facial cleansers for the entire faces continuously for 3 weeks (sample-using group).

Similarly, other five expert panelists (male) used a common facial cleanser (Biore Skin Care Facial Cleanser (moisture), manufactured by Kao Corporation) as in above, instead of the following facial cleansers (common facial cleanser-using group).

in both groups was photographed with VISIA (manufactured by Canfield Scientific, Inc.) on day 0 (before the use), day 7, day 14, and day 21 of the use, and the average luminance of internal scattered light was calculated for the skin part of the entire face. The difference of each average luminance value of the internal scattered light on day 7, day 14, and day 21 from the average luminance of the internal scattered light on day 0 was calculated, and each average amount of change in the average luminance value of internal scattered light after the use for 7 days, 14 days, and 21 days was calculated for each group. The results are shown in FIG. 1.

(Facial Cleanser)

| Component | (mass %) |
|---|---|
| 2-Amino-2-hydroxymethyl-1,3-propanediol | 5 |
| Arginine | 5 |
| POE (21) lauryl ether *6 | 0.25 |
| Myristic acid | 0.4 |
| POE (2.6) lauryl ether acetate *10 | 0.1 |
| Trehalose | 5 |
| Sorbitol | 3.9 |
| Mannitol | 10 |
| Water | 70.35 |
| pH | 10 |
| Detergency against keratotic plugs (during cleansing) | 9 |

As obvious from FIG. 1, the sample-using group showed a tendency of improving the brightness of the skin, compared to the common facial cleanser-using group.

Examples of the prescription of the present invention are shown below. All of them have effects equivalent to those of Examples described above.

Prescription Examples 1 to 3 (Facial Cleansers)

| Component | Rx 1 | Rx 2 | Rx 3 |
|---|---|---|---|
| 2-Amino-2-hydroxymethyl-1,3-propanediol | 5 | 5 | 5 |
| 2-Amino-2-methyl-1-propanol | — | 5 | — |
| 2-Amino-2-methyl-1,3-propanediol | — | — | 5 |

-continued

| Component | Rx 1 | Rx 2 | Rx 3 |
|---|---|---|---|
| Arginine | 5 | — | — |
| POE (2) sodium lauryl sulfate *1 | 1.0 | 1.0 | 1.0 |
| Sodium cocoyl glutamate | 1 | 1 | 1 |
| Lauramidopropyl betaine *11 | 0.5 | 0.5 | 0.5 |
| Glycerol | 5 | 5 | 5 |
| 1,3-Butylene glycol | 5 | 5 | 5 |
| Hydroxyethyl cellulose *12 | 0.1 | 0.1 | 0.1 |
| (Acrylate/alkyl (C10-30) acrylate) cross polymer *13 | 0.1 | 0.1 | 0.1 |
| 50% Aqueous solution of malic acid | 1 | 2 | 1 |
| Water | 70.7 | 70.7 | 70.7 |
| pH | 10 | 10 | 10 |
| Detergency against keratotic plugs (during cleansing) | 7 | 3 | 5 |

[Prescription 4 (Facial Cleanser)]

| Component | (mass %) |
|---|---|
| 2-Amino-2-hydroxymethyl-1,3-propanediol | 5 |
| Arginine | 5 |
| POE (21) lauryl ether *6 | 2 |
| Sorbitol | 10 |
| Trimethyl glycine | 10 |
| (Acrylate/alkyl (C10-30) acrylate) cross polymer *14 | 0.65 |
| Hydroxyethyl cellulose *12 | 0.08 |
| 50% Aqueous solution of malic acid | 0.8 |
| Water | 66.47 |
| pH | 10 |
| Detergency against keratotic plugs (during cleansing) | 9 |

[Prescription 5 (Body Cleanser)]

| Component | (mass %) |
|---|---|
| 2-Amino-2-hydroxymethyl-1,3-propanediol | 5 |
| Arginine | 5 |
| POE (21) lauryl ether *6 | 0.25 |
| Myristic acid | 0.4 |
| Trehalose | 5 |
| Sorbitol | 3.9 |
| Mannitol | 10 |
| (Acrylate/alkyl (C10-30) acrylate) cross polymer *14 | 0.55 |
| Hydroxyethyl cellulose *12 | 0.13 |
| Water | 66.67 |
| pH | 10 |
| Detergency against keratotic plugs (during cleansing) | 9 |

10: AKYPO LM 26C (manufactured by Kao Corporation)
11: Amphitol 20HD (manufactured by Kao Corporation)
12: HEC Daicel SE850 (manufactured by Daicel Fine-Chem Ltd.)
13: Carbopol ETD2020 polymer (manufactured by Lubrizol Advanced Materials, Inc.)
14: Carbopol Ultrez 21 polymer (manufactured by Lubrizol Advanced Materials, Inc.)

The invention claimed is:

1. A method for removing keratotic plugs, the method comprising:
applying to skin having keratotic plugs a composition comprising at least one component selected from the group consisting of (X1) 2-amino-2-hydroxymethyl-1,3-propanediol, (X2) 2-amino-2-methyl-1-propanol, and (X3) 2-amino-2-methyl-1,3-propanediol, as a component (X), and
at least one component selected from the group consisting of (B1) a nonionic surfactant having an HLB of at least 11 and (B2) a nonionic surfactant having an HLB of less than 11, as a component (B),
wherein the composition has a pH of from 9.2 to 12.5 at 25° C.,
wherein a mass ratio of a content of the component (X) to a content of the component (B), (X)/(B), is from 0.03 to 50,
wherein a content of the component (X) in the composition is from 0.5 mass % to 35 mass %, and
wherein the component (B1) comprises at least one selected from the group consisting of a polyglycerol fatty acid ester, polyethylene glycol fatty acid ester, polyoxyethylene glycerol fatty acid ester, polyoxyethylene sorbitan fatty acid ester, polyoxyethylene hydrogenated castor oil fatty acid ester, polyoxyethylene alkyl ether, and alkyl polyglucoside, and the component (B2) comprises at least one selected from the group consisting of a polyoxyethylene alkyl ether and polyglycerol fatty acid ester.

2. The method for removing keratotic plugs according to claim 1, wherein a content of the component (B) in the composition is from 0.1 mass % to 30 mass %.

3. The method for removing keratotic plugs according to claim 1, wherein the composition comprises the nonionic surfactant (B1) and the nonionic surfactant (B2) and a mass ratio of a content of the component (B1) to a content of the component (B2), (B1)/(B2), is from 0.1 to 25.

4. The method for removing keratotic plugs according to claim 1, wherein the composition further comprises (Y) a basic substance other than the component (X).

5. The method for removing keratotic plugs according to claim 1, wherein the composition further comprises from 10 mass % to 99.9 mass % of water.

6. The method for removing keratotic plugs according to claim 1, wherein the composition further comprises (A) an anionic surfactant.

7. The method for removing keratotic plugs according to claim 1, wherein the component (X) consists of (X1) 2-amino-2-hydroxymethyl-1,3-propanediol.

8. The method for removing keratotic plugs according to claim 1, wherein the component (X) consists of (X2) 2-amino-2-methyl-1-propanol.

9. The method for removing keratotic plugs according to claim 1, wherein the component (X) consists of (X3) 2-amino-2-methyl-1,3-propanediol.

10. The method for removing keratotic plugs according to claim 1, further comprising:
applying the composition to the skin; and
after a certain period of time, washing away the composition with water or wiping away the composition with a wiping material.

11. A method for removing keratotic plugs, the method comprising:
applying to skin having keratotic plugs a composition comprising at least two components selected from the group consisting of (X1) 2-amino-2-hydroxymethyl-1,3-propanediol, (X2) 2-amino-2-methyl-1-propanol, and (X3) 2-amino-2-methyl-1,3-propanediol, as a component (X), and
at least one component selected from the group consisting of (B1) a nonionic surfactant having an HLB of at least 11 and (B2) a nonionic surfactant having an HLB of less than 11, as a component (B),
wherein the composition has a pH of from 9.2 to 12.5 at 25° C., wherein a mass ratio of a content of the component (X) to a content of the component (B), (X)/(B), is from 0.03 to 50, wherein a content of the component (X) in the composition is from 0.5 mass % to 35 mass %, and wherein the component (B1) comprises at least one selected from the group consisting of a polyglycerol fatty acid ester, polyethylene glycol fatty acid ester, polyoxyethylene glycerol fatty acid ester, polyoxyethylene sorbitan fatty acid ester, polyoxyethylene hydrogenated castor oil fatty acid ester, polyoxyethylene alkyl ether, and alkyl polyglucoside, and the component (B2) comprises at least one selected from the group consisting of a polyoxyethylene alkyl ether and polyglycerol fatty acid ester.

12. The method for removing keratotic plugs according to claim 11, wherein the component (X) comprises (X3) 2-amino-2-methyl-1,3-propanediol and at least one component selected from the group consisting of (X1) 2-amino-2-hydroxymethyl-1,3-propanediol and (X2) 2-amino-2-methyl-1-propanol.

13. The method for removing keratotic plugs according to claim 11, wherein a content of the component (B) in the composition is from 0.1 mass % to 30 mass %.

14. The method for removing keratotic plugs according to claim 11, wherein the composition comprises the nonionic surfactant (B1) and the nonionic surfactant (B2) and a mass ratio of a content of the component (B1) to a content of the component (B2), (B1)/(B2), is from 0.1 to 25.

* * * * *